United States Patent
Sato

(10) Patent No.: US 7,316,059 B2
(45) Date of Patent: Jan. 8, 2008

(54) METHOD OF MANUFACTURING AN ULTRASONIC PROBE

(75) Inventor: Shohei Sato, Tokyo (JP)

(73) Assignee: Aloka Co., Ltd., Tokyo (JP)

( * ) Notice: Subject to any disclaimer, the term of this patent is extended or adjusted under 35 U.S.C. 154(b) by 63 days.

(21) Appl. No.: 11/334,830

(22) Filed: Jan. 19, 2006

(65) Prior Publication Data

US 2006/0119222 A1  Jun. 8, 2006

Related U.S. Application Data

(62) Division of application No. 10/620,094, filed on Jul. 15, 2003, now Pat. No. 7,148,607.

(30) Foreign Application Priority Data

| Jul. 19, 2002 | (JP) | ............................ 2002-210891 |
| Jun. 13, 2003 | (JP) | ............................ 2003-169658 |
| Jun. 13, 2003 | (JP) | ............................ 2003-169659 |

(51) Int. Cl.
*H04R 3/00* (2006.01)

(52) U.S. Cl. .................. 29/594; 29/25.35; 29/417; 29/602.1; 29/609.1; 310/328; 310/333; 310/365; 310/367; 347/70; 347/71; 347/72

(58) Field of Classification Search ............... 29/25.35, 29/417, 592.1, 594, 602.1, 609, 609.1, 856, 29/868; 83/169; 310/328, 333, 335–337, 310/365–367; 347/70–72
See application file for complete search history.

(56) References Cited

U.S. PATENT DOCUMENTS 5,329,496 A  7/1994  Smith
5,548,564 A  8/1996  Smith
5,704,105 A  1/1998  Venkataramani et al.
5,834,880 A * 11/1998  Venkataramani et al. ... 310/334

(Continued)

FOREIGN PATENT DOCUMENTS

EP  1 132 978  9/2001

(Continued)

OTHER PUBLICATIONS

M. Zipparo et al., "Medical imaging phased arrays using multilayer ceramics and composites", *2000 IEEE Ultrasonics Symposium*.

(Continued)

*Primary Examiner*—Paul D. Kim
(74) *Attorney, Agent, or Firm*—William L. Androlia; H. Henry Koda

(57) ABSTRACT

A method of manufacturing an ultrasonic probe including the steps of forming a plurality of first slits on a layered assembly having a first inner electrode member and a second inner electrode member through a top surface of the layered assembly and forming a plurality of second slits through a bottom surface of the layered assembly, forming a first vertical electrode layer on each side surface within each of the first slits, forming a second vertical electrode layer on each side surface within each one of the second slits and forming a plurality of separating slits on the layered assembly to divide the layered assembly into a plurality of transducer elements.

7 Claims, 25 Drawing Sheets

12A, 14A, 16A PIEZOELECTRIC LAYER
42A TOP ELECTRODE LAYER
18B, 20B INNER ELECTRODE LAYER
44A BOTTOM ELECTRODE LAYER
60A ELECTRODE PAD

U.S. PATENT DOCUMENTS

| | | |
|---|---|---|
| 5,945,770 A | 8/1999 | Hanafy |
| 6,049,159 A | 4/2000 | Barthe et al. |
| 6,088,894 A | 7/2000 | Oakley et al. |
| 6,429,574 B1 | 8/2002 | Mohr, III et al. |
| 6,437,487 B1 | 8/2002 | Mohr, III et al. |
| 6,441,538 B1 | 8/2002 | Spigelmyer |
| 6,483,228 B2 | 11/2002 | Hashimoto |
| 6,664,717 B1 | 12/2003 | Mohlr et al. |
| 2002/0073781 A1 | 6/2002 | Hashimoto et al. |
| 2002/0130590 A1 | 9/2002 | Shiraishi et al. |

FOREIGN PATENT DOCUMENTS

| | | |
|---|---|---|
| JP | 62-22634 | 1/1987 |
| JP | 5-37998 | 2/1993 |
| JP | 5-228142 | 9/1993 |
| JP | 11-299779 | 11/1999 |
| JP | 2000-138400 | 5/2000 |
| JP | 2001-29346 | 2/2001 |
| JP | 2001102651 A * | 4/2001 |
| JP | 2002-112397 | 4/2002 |

OTHER PUBLICATIONS

M. Zipparo et al., "Multilayer ceramics and composites for ultrasonic imaging arrays", *1999 IEEE Ultrasonics Symposium*, 947-952.

Oakley et al., "A 2.5 MHz phased linear array made from stacked piezoelectric composite", *1998 IEEE Ultrasonics Symposium*, 999-1002.

Oakley et al., "Stacked composite piezoelectric materials for 1.5-D arrays", *1997 IEEE Ultrasonics Symposium*, 923-926.

David M. Mills et al., "Combining multi-layers and composites to increase SNR for medical ultrasound transducers", *1996 IEEE Ultrasonics Symposium*, 1509-1512.

* cited by examiner 12A, 14A, 16A PIEZOELECTRIC LAYER   44A BOTTOM ELECTRODE LAYER
42A TOP ELECTRODE LAYER            60A ELECTRODE PAD
18B, 20B INNER ELECTRODE LAYER

METHOD OF MANUFACTURING AN ULTRASONIC PROBE

This is a division of application Ser. No. 10/620,094 filed Jul. 15, 2003, now U.S. Pat. No. 7,148,607.

BACKGROUND OF THE INVENTION

1. Field of the Invention

The present invention relates to an ultrasonic probe and a method of manufacturing an ultrasonic probe, and more particularly to a structure of a layered array transducer for use in ultrasonic diagnosis of a living body and a method of manufacturing the same.

2. Description of Related Art 2D array transducers (including sparse 2D array transducers) and 1.5D array transducers are known as array transducers having a plurality of transducer elements arranged in an array. In these array transducers, because the size of each transducer element forming an array transducer is very small, the electrical impedance of each transducer element is very high and this prohibits electrical impedance match between each transducer element and a cable (or an apparatus body). This causes significant loss of sensitivity.

In order to deal with the above problem, a technique of forming each transducer element into a layered structure has been proposed. According to this technique, each transducer element is made up of a plurality of piezoelectric layers and a plurality of electrode layers which are laminated in a predetermined order to form a layered assembly. More specifically, a bottom electrode layer and a top electrode layer are provided on the bottom and top surfaces of a layered assembly, respectively, and an inner electrode layer is formed between two adjacent piezoelectric layers. The odd numbered electrode layers in these electrode layers function as signal electrode layers, for example, whereas the even numbered electrode layers function as ground electrode layers, for example. A voltage signal is applied between a plurality of signal electrode layers and a plurality of ground electrode layers. With this structure, it is possible to reduce the electrical impedance of the transducer elements.

The layered transducer elements as described above, however, have a problem of electrical connection with regard to a plurality of electrode layers, in particular, a problem of how a lead or the electrode layer is connected to a plurality of inner electrode layers. According to one example method conventionally used, a via (a thin conductive line passing through the center, for example, of the transducer element in the vertical direction) is used for such connection. This method, however, also has a problem that because the area of the transducer element is very small, applying any process to a completed transducer element is difficult in terms of manufacturing and is not practical.

Japanese Patent Laid-Open Publication No. 2001-29346 discloses an array transducer comprising a plurality of layered transducer elements. In the array transducer disclosed in this publication, in order to eliminate or reduce the above-described problem of the conventional art, a ground side electrode layer connected to a ground inner electrode is formed on a first side surface of each layered transducer element whereas a signal side electrode layer connected to a signal inner electrode layer is formed on a second side surface (opposite to the first side surface) of each layered transducer element. When attention is paid to two adjacent transducer elements in such an array transducer, the signal side electrode layer of one transducer element and the ground side electrode layer of the other transducer element are adjacent to each other and are formed in such a manner that they are shifted from each other in the vertical direction. In order to enhance characteristics of the array transducer, it is desired that electrical insulation be further increased. It is also desirable to increase the positioning accuracy and simplify fabrication of an array transducer (such as simultaneous formation of a pair of opposing side electrode layers, for example). Further, it is desirable to appropriately generate an electric field in each transducer element.

SUMMARY OF THE INVENTION

An advantage of the present invention is that it provides an ultrasonic probe having a layered array transducer with excellent performance and a method of manufacturing such an ultrasonic probe.

Another advantage of the present invention is that it simplifies manufacture of an ultrasonic probe having a layered array transducer.

(1) In accordance with one aspect of the present invention, there is provided an ultrasonic probe comprising a layered ultrasonic transducer having a first part and a second part which are adjacent to each other, wherein each of the first part and the second part includes a plurality of first horizontal electrode layers and a plurality of second horizontal electrode layers alternately provided in the vertical direction; a first vertical electrode layer electrically connected with the plurality of first horizontal electrode layers; and a second vertical electrode layer electrically connected with the plurality of second horizontal electrode layers, the first vertical electrode layer included in the first part and the first vertical electrode layer included in the second part being adjacent to each other via a first gap region and having the same polarity, and the ultrasonic transducer includes a first specified structure formed by the first vertical electrode layer included in the first part, the first vertical electrode layer included in the second part, and the first gap region.

With the above structure, the ultrasonic transducer is a 1D array transducer, a 1.5D array transducer, a 2D array transducer or the like. The first part and the second part, each having a layered structure, are adjacent to each other in the horizontal direction. Namely, the first and second parts correspond to two adjacent layered transducer elements or two segments or blocks interconnected in the horizontal direction in a certain layered transducer element. The first specified structure is formed across (or between) the first and second parts. The first specified structure has a function of connecting a ground line or a signal line to a plurality of first horizontal electrode layers included in the first and second parts. The first specified structure comprises a pair of first vertical electrode layers (the first vertical electrode layer of the first part and the first vertical electrode layer of the second part) which face each other with a space interposed therebetween. Because the pair of the first vertical electrode layers have the same polarity (ground or signal), electrical performance such as insulation property can be advantageously enhanced. A reinforcing layer, an insulating layer, a resin layer used for compounding, an element separation layer, or the like may be provided in the first gap region. Each vertical electrode layer functions as a side electrode, an inner electrode, or the like. While it is desirable to form each vertical electrode layer in the form of a plane, other forms may also be adopted. The array transducer may have a convex shape. In this case, for each transducer element, the vertical direction is defined as the ultrasound propagation direction.

Preferably, the above ultrasonic transducer further comprises a third part adjacent to the second part, the third part including a plurality of first horizontal electrode layers and a plurality of second horizontal electrode layers alternately provided in the vertical direction; a first vertical electrode layer electrically connected with the plurality of first horizontal electrode layers; and a second vertical electrode layer electrically connected with the plurality of second horizontal electrode layers, the second vertical electrode layer included in the second-part and the second vertical electrode layer included in the third part being adjacent to each other via a second gap region and having the same polarity, and the ultrasonic transducer includes a second specified structure formed by the second vertical electrode layer included in the second part, the second vertical electrode layer included in the third part, and the second gap region.

With the above structure, the first part, the second part, and the third part are arranged in the horizontal direction. The first specified structure is formed across (or between) the first and second parts, and the second specified structure is formed across (or between) the second and third parts. The first specified structure and the second specified structure have different polarities. In the second specified structure, similar to the first specified structure, a pair of the second vertical electrode layers having the same polarity face each other via the second gap region.

Preferably, each of the first specified structure and the second specified structure is configured symmetrically in the horizontal direction. Preferably, the first specified structure and the second specified structure are mutually inverted in the vertical direction.

Each of the above-described specified structures (the first specified structure and the second specified structure) has a pair of vertical electrode layers having the same polarity, which are adjacent and face each other. In this regard, the specified structure can also be referred to as a "face-to-face structure" or a "side-by-side structure". While the specified structure may be asymmetric in the horizontal direction, it is desirable that the specified structure is formed in a symmetrical structure or a mirror structure in the horizontal direction for ease of manufacturing. Each specified structure can be easily fabricated using a repeating slit formation, material filling, or the like, for example.

Preferably, each of the first part, the second part, and the third part further comprises a piezoelectric section including the plurality of first horizontal electrode layers, the plurality of second horizontal electrode layers, and a plurality of piezoelectric layers; first insulating means formed on one side of the piezoelectric section for insulating the first vertical electrode layer with respect to the plurality of second horizontal electrode layers; and second insulating means formed on the other side of the piezoelectric section for insulating the second vertical electrode layer with respect to the plurality of first horizontal electrode layers.

With the above structure, by providing the first insulation means and the second insulation means, it is possible to achieve insulation which is necessary for each polarity of signal and ground and also to prevent or reduce disturbance or distortion of electric field within the piezoelectric section (more accurately, the piezoelectric section body formed by a plurality of piezoelectric layers and a plurality of horizontal electrode layers), which can be caused by the pair of vertical electrode layers. It is therefore possible to achieve good electromechanical conversion efficiency in the piezoelectric section.

Due to compounding or compositing of the array transducer, one or more advantages, including that acoustic impedance of each transducer element can be adjusted (preferably reduced) and that the frequency band can be adjusted (preferably enlarged), can be obtained.

(2) In accordance with another aspect of the present invention, there is provided an ultrasonic probe comprising an array transducer including a plurality of transducer elements, wherein each of the transducer elements comprises a plurality of first horizontal electrode layers and a plurality of second horizontal electrode layers which are provided alternately in the Z direction; a first vertical electrode layer electrically connected with the plurality of first horizontal electrode layers; and a second vertical electrode layer electrically connected with the plurality of second horizontal electrode layers, the array transducer comprises a plurality of first specified structures and a plurality of second specified structures which are alternately provided in the X direction, in each of the first specified structures, two first vertical electrode layers of two adjoining transducer elements are adjacent to each other via a first gap region, and in each of the second specified structures, two second vertical electrode layers of two adjoining transducer elements are adjacent to each other via a second gap region.

With the above structure, a plurality of the first specified structures and a plurality of the second specified structures are alternately formed in the X direction. When attention is paid to two transducer elements adjacent to each other in the X direction, the vertical electrode layer of one transducer element and the vertical electrode layer on the other transducer element are adjacent and face each other, and have the same polarity. This configuration is therefore advantageous in terms of insulation or withstand voltage property.

Preferably, each of the transducer elements further comprises first insulating means for electrically insulating the first vertical electrode layer with respect to the plurality of second horizontal electrode layers, and second insulating means for electrically insulating the second vertical electrode layer with respect to the plurality of first horizontal electrode layers. Here, preferably, the first insulating means comprises a first vertical insulating layer, and the second insulating means comprises a second vertical insulating layer.

With the above structure, the first vertical electrode layer is insulated from a plurality of the second horizontal electrode layers by the first insulating means, and the second vertical electrode layer is insulated from a plurality of the first horizontal electrode layers by the second insulating means. By providing the first and second insulating means, disturbance of electric field within the elements which may be caused by the presence of each vertical electrode layer can be prevented or reduced.

There is a possibility that polarization of the piezoelectric materials will be decreased or lost in the process of manufacturing an array transducer due to temperature increase or the like. In such a case, a re-polarization process is additionally performed. When performing the re-polarization process, the presence of the first and second insulating means decreases the occurrence of polarization distortion. This effect becomes greater as the relative dielectric constant of the material of the first and second insulating means becomes smaller compared to the relative dielectric constant of the material of the transducer elements. Preferably, the ratio is approximately 1/1000, for example.

(3) In accordance with another aspect of the present invention, there is provided an ultrasonic probe comprising an array transducer including a plurality of transducer elements, wherein each of the transducer elements comprises at least one piezoelectric section and at least one resin section which are coupled in the horizontal direction, the at least one piezoelectric section including a plurality of piezoelectric layers and a plurality of horizontal electrode layers which are laminated in a predetermined order in the vertical direction and a pair of vertical electrode layers which are electrically connected to the plurality of horizontal electrode layers so as to establish a predetermined connection relationship with the plurality of horizontal electrode layers, the at least one resin section being formed as a filler layer having continuity in the vertical direction, and wherein each of the transducer elements is vertically layered and is compounded in the horizontal direction.

With the above structure, each transducer element is composite element, and comprises at least one layered piezoelectric section and at least one resin section. Because the resin section is formed as a filler layer which is continuous in the vertical direction, and is not subdivided into individual layers in the vertical direction, a positioning error in the horizontal direction is basically not caused. Further, because the resin section is formed as a filler layer, the resin section can be easily formed by forming a slit and filling the slit with a filler material in a layered assembly which has been already formed. In such a case, a problem of positioning error in the horizontal direction for a plurality of layers which form the layered piezoelectric section can also be eliminated.

(4) A method of manufacturing an ultrasonic probe in accordance with an aspect of the present invention comprises the steps of forming a plurality of first slits on a layered assembly having a first inner electrode member and a second inner electrode member through a top surface of the layered assembly and forming a plurality of second slits through a bottom surface of the layered assembly such that they are parallel to and alternate with the plurality of first slits; forming a first vertical electrode layer on each side surface within each of the first silts, the first vertical electrode layer being electrically connected with the first inner electrode member and being insulated with respect to the second inner electrode member, thereby forming a plurality of first specified structures corresponding to the plurality of first silts; forming a second vertical electrode layer on each side surface within each of the second silts, the second vertical electrode layer being electrically connected with the second inner electrode member and being insulated with respect to the first inner electrode member, thereby forming a plurality of second specified structures corresponding to the plurality of second silts; and after formation of the plurality of first specified structures and the plurality of second specified structures, forming a plurality of separating slits on the layered assembly, thereby dividing the layered assembly into a plurality of transducer elements.

With the above structure, by repeating formation of slits and filling of the slits with regard to a layered assembly in steps, a plurality of the first specified structures and a plurality of the second specified structures are alternately formed in the horizontal direction. It is therefore possible to simplify the manufacturing process and to prevent a positioning error in the horizontal direction between laminated members.

While composite or compound ultrasonic transducers generally have an advantage of wide frequency band, they suffer from a problem that electrical impedance is increased and the sensitivity is reduced. According to the above method, by performing compounding and lamination with respect to an ultrasonic transducer, an ultrasonic transducer with a wide frequency band can be achieved while the electrical impedance of the transducer being decreased. As a result, the sensitivity of the ultrasonic transducer can be increased. Further, because compounding is performed after lamination, it is possible to eliminate or reduce a problem of positioning error in the horizontal direction among the laminated members. Thus, the performance of the ultrasonic transducer can be enhanced.

(5) A method of manufacturing an ultrasonic probe in accordance with another aspect of the present invention comprises the steps of forming a plurality of first slits having a first depth on a layered assembly comprising a first inner electrode member and a second inner electrode member through a top surface of the layered assembly; forming a plurality of second slits having a second depth on the layered assembly through a bottom surface of the layered assembly, such that the plurality of second slits are parallel to and alternate with the plurality of first slits; filling the plurality of first slits and the plurality of second slits with an insulating material and hardening the insulating material; forming a plurality of third slits by cutting through the insulating material within the plurality of first slits, the plurality of third slits having a width which allows the insulating material which is hardened to be left on each side surface of each of the first slits and having a third depth which is greater than the first depth; forming a plurality of fourth slits by cutting through the insulating material within the plurality of second slits, the plurality of fourth slits having a width which allows the insulating material which is hardened to be left on each side surface of each of the second slits and having a fourth depth which is greater than the second depth; forming a first vertical electrode layer electrically connected with the first inner electrode member on each side surface of each of the third slits, thereby forming a plurality of first specified structures on the layered assembly; forming a second vertical electrode layer electrically connected with the second inner electrode member on each side surface of each of the fourth slits, thereby forming a plurality of second specified structures on the layered assembly; after formation of the plurality of first specified structures and the plurality of second specified structures, forming a top electrode member on a top surface of the layered assembly and forming a bottom electrode member on a bottom surface of the layered assembly; bonding a backing to the bottom electrode member; and after bonding of the backing, dividing the layered assembly into a plurality of transducer elements.

BRIEF DESCRIPTION OF THE DRAWINGS

These and other objects of the invention will be explained in the description below, in connection with the accompanying drawings, in which.

DETAILED DESCRIPTION OF THE PREFERRED EMBODIMENT

Preferred embodiments of the present invention will be described in further detail with reference to the accompanying drawings.

Figure 1:
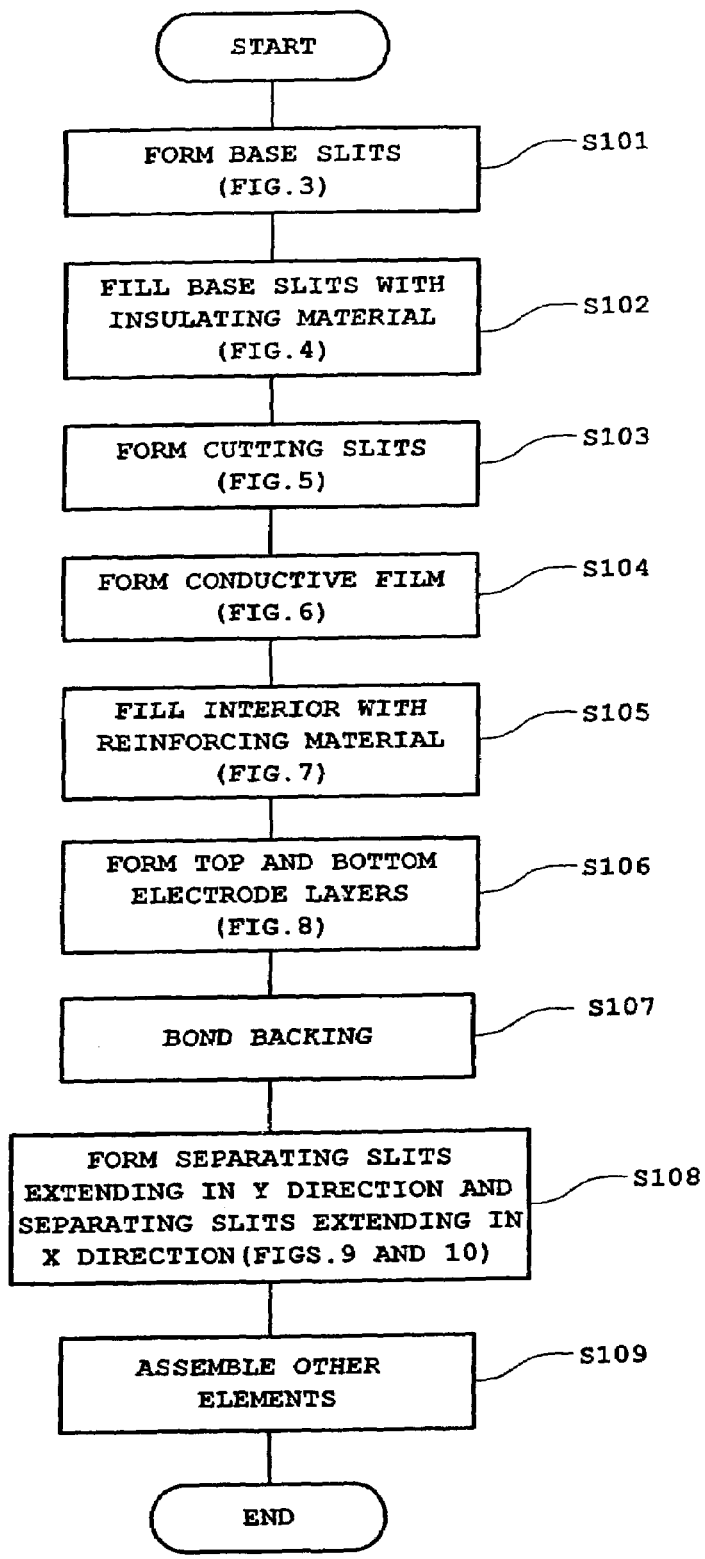
FIG. 1 is a flow chart for explaining a first example process of manufacturing an ultrasonic probe according to the present invention.

FIG. 1 shows one example manufacturing process for an ultrasonic probe in the form of flow chart. This ultrasonic probe is a probe connected via a probe cable to an ultrasonic diagnosis apparatus which provides ultrasonic diagnosis of a living body and captures echo data by ultrasound transmission/reception. The ultrasonic probe may be used in contact with a surface of a living body or may be inserted into a body cavity of a living body. A manufacturing process of such an ultrasonic probe will be described, along with the structural features of the ultrasonic probe (particularly of an array transducer).

Figure 2:
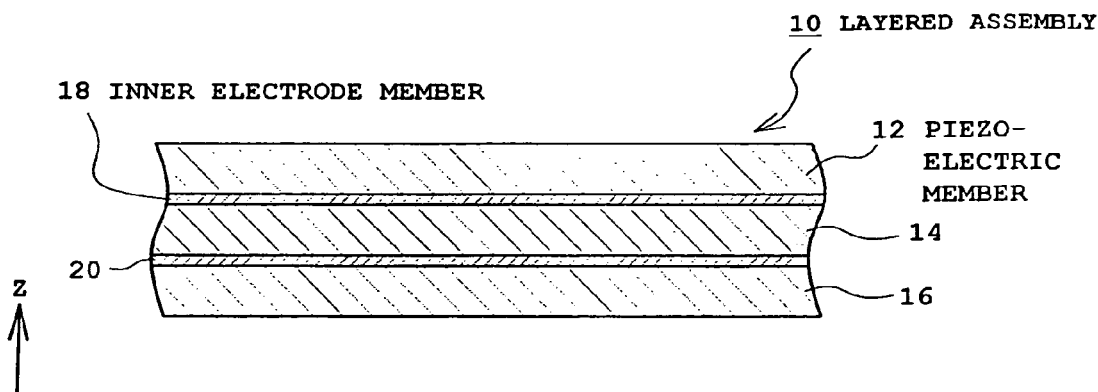
FIG. 2 is a cross sectional view showing a layered assembly.

Prior to step S101 of FIG. 1, a laminated unit (a layered assembly) to which polarization has been applied as shown in FIG. 2 is provided. A plurality of members forming the layered assembly are previously bonded to each other. More specifically, the layered assembly 10 has a plate-like shape as a whole as shown in FIG. 1, and comprises a plurality of piezoelectric members 12, 14, and 16. Between two adjacent piezoelectric members 12 and 14 (14 and 16), inner electrode members 18, 20 are provided as horizontal electrode members. The size of the layered assembly 10 is, for example, 20 mm in the X direction, 20 mm in the Y direction, and 0.51 mm in the Z direction. The piezoelectric members 12, 14, 16 may be formed of a known piezoelectric material such as PZT, or may of course be formed of other materials (such as a composite material). In FIGS. 2 to 9, the X direction (the first horizontal direction) corresponds to the left-right direction in the drawings and the Z direction (the vertical direction) corresponds to the upper-lower direction of the drawings. The Z direction also corresponds to the ultrasound transmission/reception direction.

Figure 3:
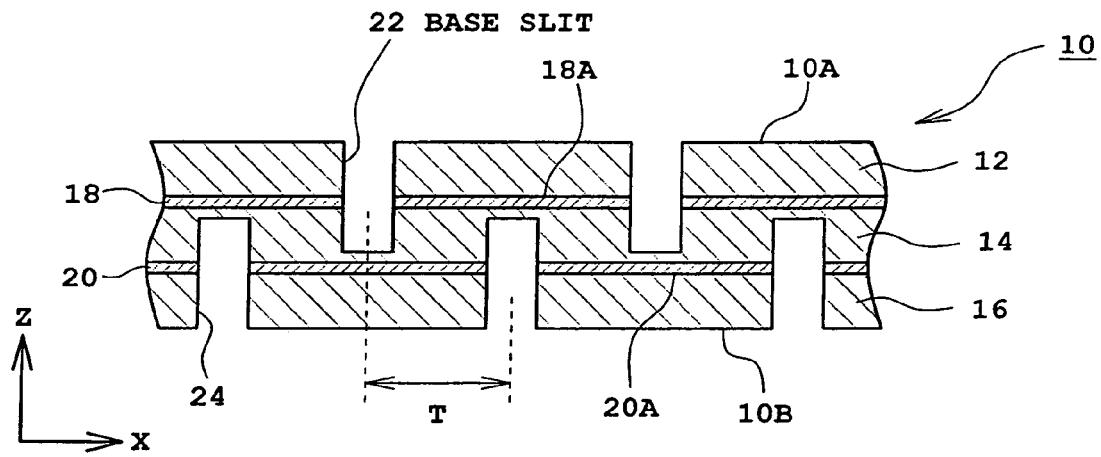
FIG. 3 is a cross sectional view showing a layered assembly in which base slits are formed.

At step S101 in FIG. 1, a plurality of base slits 22, 24 are formed as shown in FIG. 3. More specifically, on the top surface 10A side of the layered assembly 10, a plurality of base slits (first slits) 22 are formed at fixed intervals (pitch) in the X direction. In this case, the pitch of a plurality of base slits 22 is twice the pitch T of a plurality of transducer elements. Similarly, on the bottom surface 10B side of the layered assembly 10, a plurality of base slits (second slits) 24 are formed at fixed intervals (pitch) in the X directions. The pitch of a plurality of base slits 24 is also twice the pitch T of a plurality of transducer elements. Here, the plurality of base slits 22 and the plurality of base slits 24 are formed alternately in the X direction. The plurality of base slits 22 and the plurality of base slits 24 are both rectangular slits extending in the Y direction, and are therefore parallel to each other. The width W1 of the base slits 22, 24 may be set to an any appropriate size as long as a specified structure (a face-to-face structure or a side-by-side structure, as shown by numerals 200U and 200D in FIG. 9), which will be described below, can be created, and may be 0.08 mm, for example. The layered assembly 10 generally comprises n piezoelectric members which are layered, where n is preferably an odd number, and is more preferably 3.

The depth L1 of each base slit 22 extends to a point before the second inner electrode member 20 when seen from the top surface 10A, and is 0.3 mm, for example. Similarly, the depth L1 of each base slit 24 extends to a point before the second inner electrode member 18 seen from the bottom surface 10B. With the formation of these base slits 22, 24, the inner electrode member 18 is divided into a plurality of elements 18A, and the inner electrode member 20 is similarly divided into a plurality of elements 20A. For formation of the base slits 22, 24, a cutting tool such as a dicing saw may be used. Such a cutting tool may be similarly used for forming various slits described below.

Figure 4:
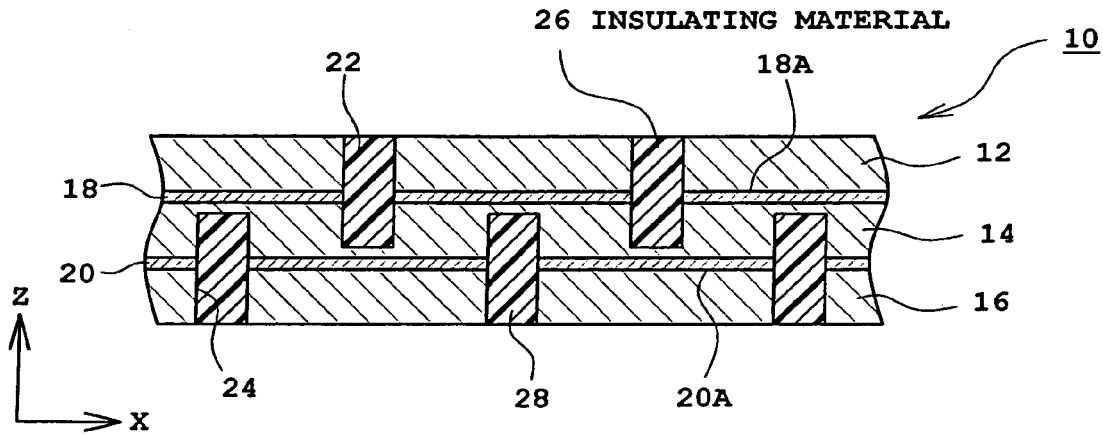
FIG. 4 is a cross sectional view showing a layered assembly in which the slits are filled with an insulating material.

At step S102 of FIG. 1, a plurality of base slits 22, 24 formed at step S101 are filled with an insulating material 26, 28 as shown in FIG. 4. The insulating material 26, 28 is preferably a material which has a high withstand voltage level even when it is formed into a thin layer, and may be a thermosetting resin such as a polyimide resin or an epoxy resin. In FIG. 4, each base slit 22 is filled with the insulating material 26 and each base slit 24 is filled with the insulating material 28.

Figure 5:
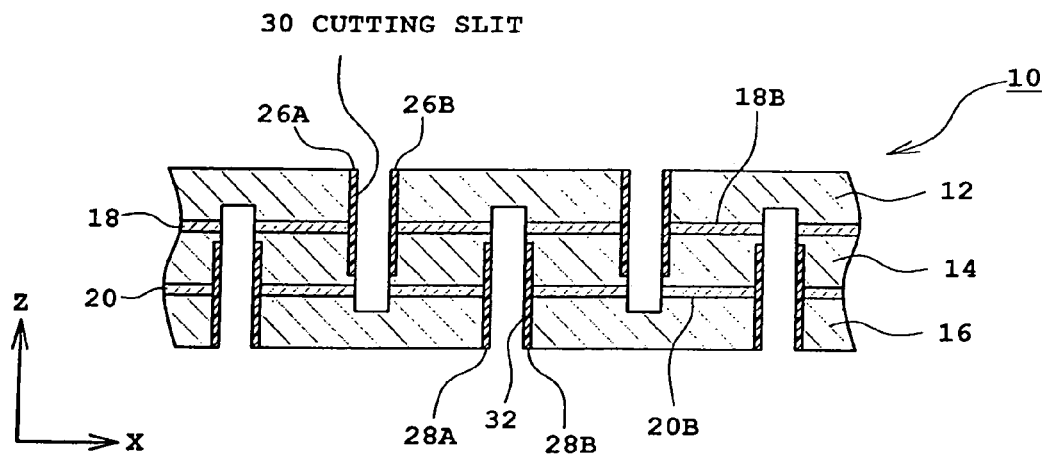
FIG. 5 is a cross sectional view showing a layered assembly in which cutting slits are formed.

At step S103, cutting slits (the third and fourth slits) 30, 32 are formed corresponding to the base slits 22, 24, respectively, as shown in FIG. 5. More specifically, in FIG. 5, the cutting slit 30 is formed by cutting through the center part of the insulating material 26 filling each base slit 22. Similarly, the cutting slit (the connecting or fourth slit) 32 is formed so as to penetrate through the center part of the insulating material 28 filling each base slit 24. The width W2 of each cutting slit 30, 32 is smaller than the width W1 of the above-described base slit 22, 24, and is 0.04 mm, for example. Further, the depth L2 of the cutting slit 30 is set to extend beyond the depth L1 of the base slit 22 so as to cut through the second inner electrode member 20 seen from the top surface, and is 0.36 mm, for example. The depth L2 of the cutting slit 32 is similarly set to penetrate through the second inner electrode member 18 seen from the bottom surface. With the formation of these cutting slits 30, 32, a side insulating layer 26A, 26B, 28A, 28B having a predetermined thickness is left on each side surface inside each base slit 22, 24. Further, with the formation of the cutting slits 30, 32, each of the above-described sections 18A, 20A (see FIG. 5) is further divided into two parts. More specifically, a plurality of inner electrode layers 18B, 20B are formed as horizontal electrode layers. It should be noted that in the above-described steps S102 to S103, formation of an insulating film using CVD or the like may be performed instead.

In the step shown in FIG. 5, when the depth of each cutting slit 30, 32 is set too large, the layered assembly 10 itself is split into pieces. It is therefore preferable to set the depth L2 of each cutting slit 30, 32 such that the layered assembly 10 retains its integrity.

Figure 6:
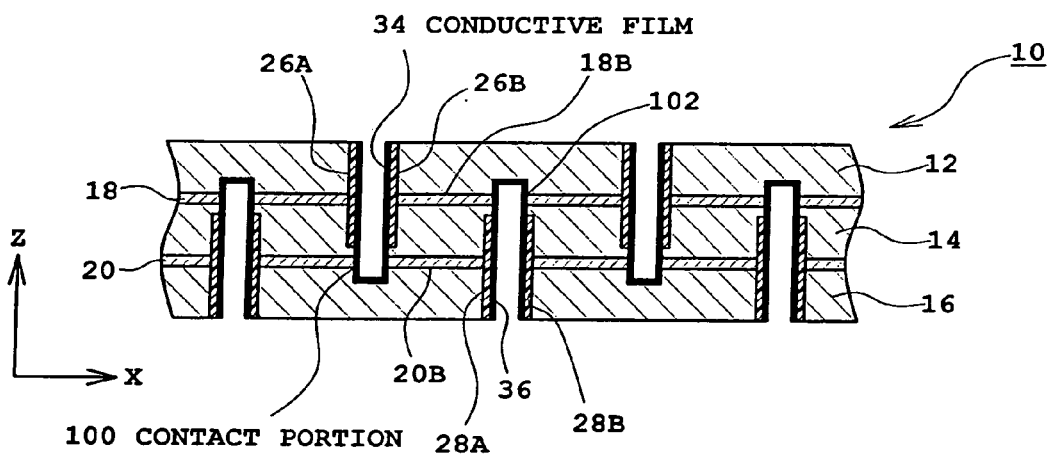
FIG. 6 is a cross sectional view showing a layered assembly in which conductive films are formed.

At step S104 of FIG. 1, a sheet-like conductive film 34, 36 is formed over each side surface within each cutting slit 30, 32 (see FIG. 6). The conductive film 34, 36 may be formed by using electroless plating and vacuum deposition, for example. Each of the conductive films 34, 36 will ultimately form a pair of vertical electrode layers (such as side electrode layers). At the manufacturing stage shown in FIG. 6, the conductive film 34 is electrically connected to the inner electrode layer 20B via a contact part 100 and is insulated from the inner electrode layer 18B by the vertical insulating layers 26A and 26B. Similarly, the conductive film 36 is electrically connected with the inner electrode layer 18B via a contact part 102. Alternatively, at the manufacturing step shown in FIG. 6, the conductive films 34, 36 may be formed by filling the cutting slits 30, 32 with a conductive member and performing a necessary cutting process.

Figure 7:
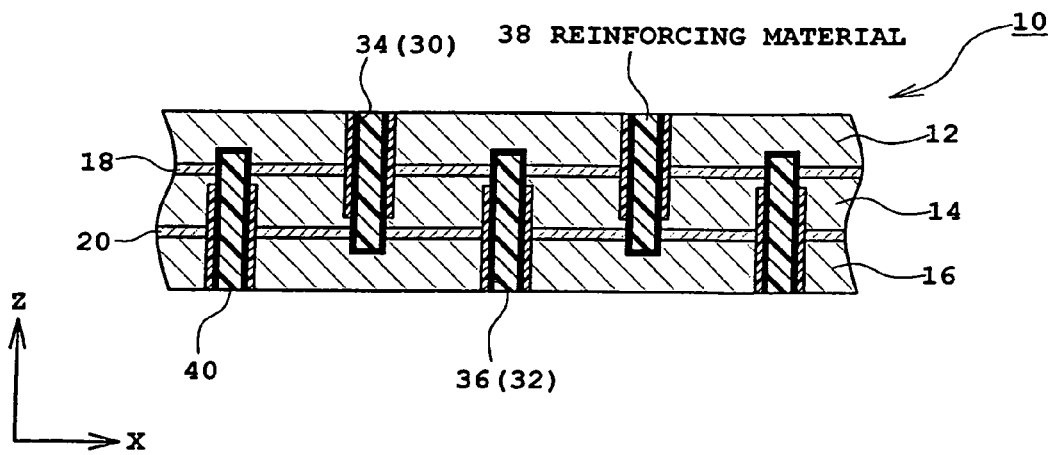
FIG. 7 is a cross sectional view showing a layered assembly in which the slits are filled with a reinforcing material.

At step S105 shown in FIG. 1, the interior of each cutting slit 30, 32, more specifically a space enclosed by each conductive film 34, 36, is filled with a reinforcing material 38, 40 (see FIG. 7). The reinforcing material 38, 40 serves as a member which covers the conductive films 34, 36 for protection. The reinforcing material 38 is formed of an insulating material, and is preferably formed by a macromolecular material, polymer material, resin material or the like having thermosetting properties. Further, this reinforcing material 38, 40 may be used as a material for compounding, as will be detailed below.

Figure 8:
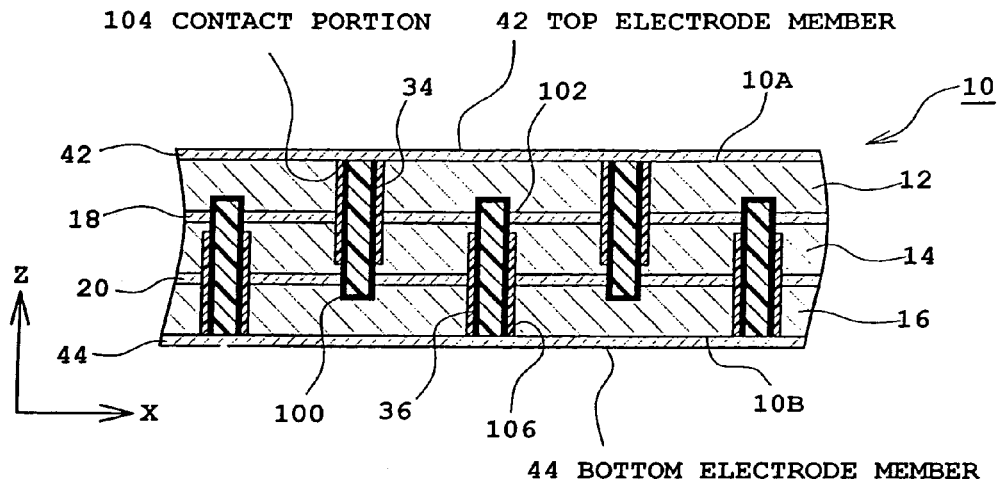
FIG. 8 is a cross sectional view showing a layered assembly having a top electrode member and a bottom electrode member provided thereon.

At step S106 of FIG. 1, an abrading treatment is first applied to the top surface 10A and the bottom surface 10B of the layered assembly 10 so as to planarize these surfaces, as shown in FIG. 8. With this treatment, the end surfaces of the conductive film 34 and 36 are appropriately exposed toward the upper and lower directions, respectively. Then, a top electrode member 42 and a bottom electrode member 44 are formed to have a predetermined thickness with respect to the top surface 10A and the bottom surface 10B, respectively, using sputtering or vacuum evaporation. In this case, the end surface of each conductive film 34 is electrically connected with the top electrode member 42 via a contact part 104, while the end surface of each conductive film 36 is electrically connected with the bottom electrode member 44 via a contact part 106.

At step S107 of FIG. 1, a backing is bonded to the layered assembly 10 on the bottom surface side. As will be described below, the backing 51 comprises a number of signal lines formed therein and is bonded to the layered assembly 10 using a conductive adhesive, for example.

Figure 9:
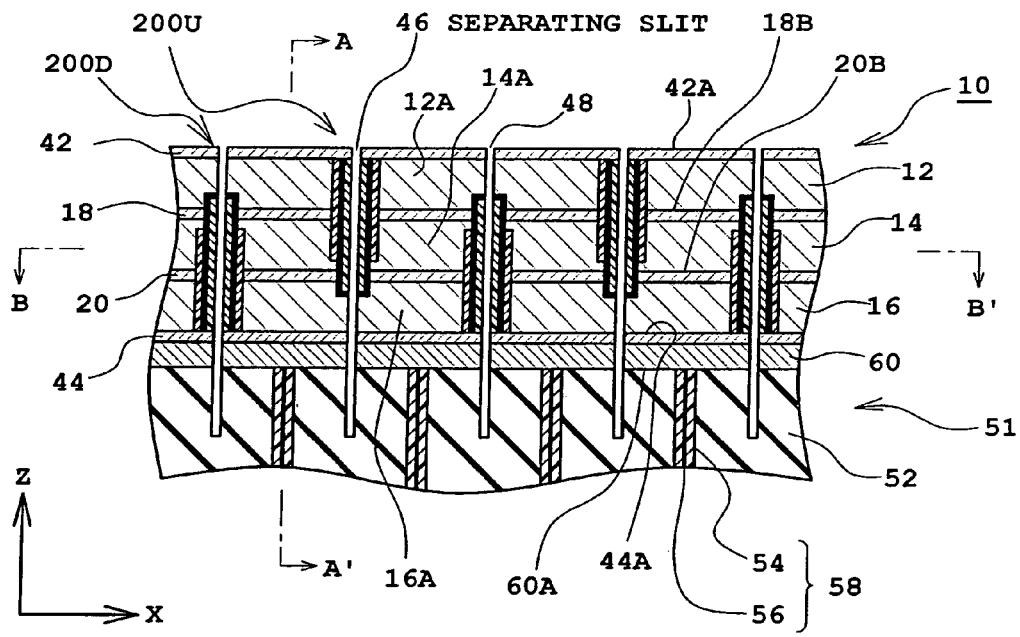
FIG. 9 is a cross sectional view showing a X-Z section of an array transducer.
Figure 10:
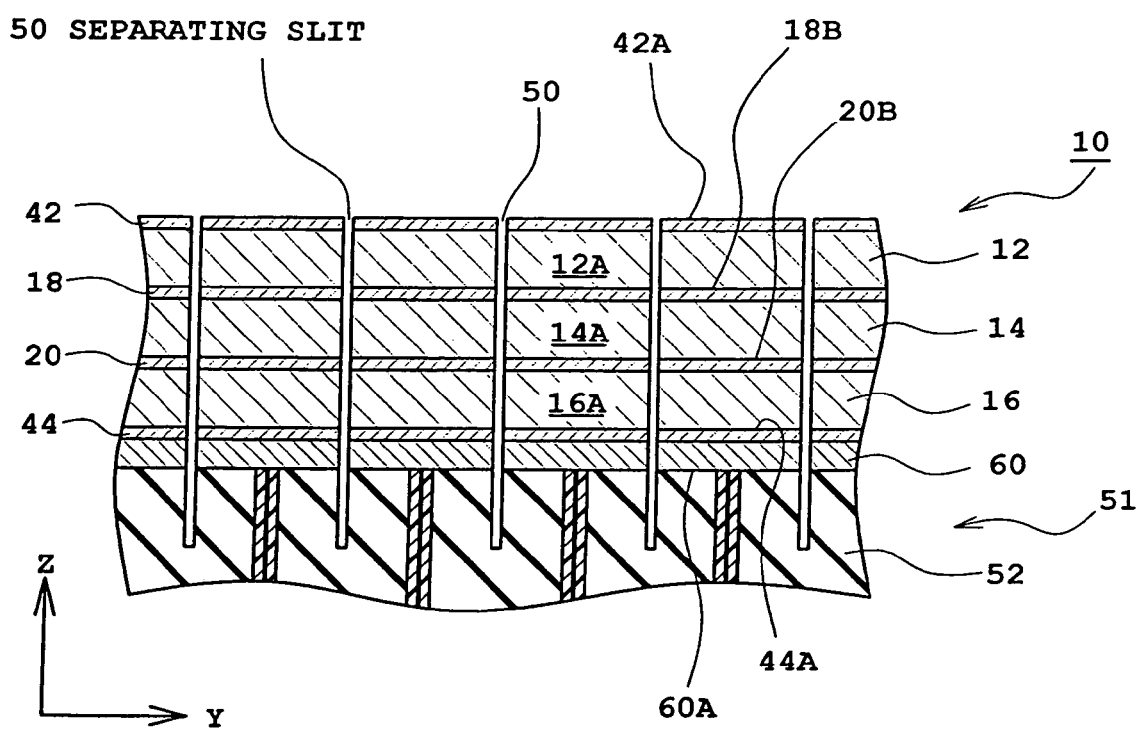
FIG. 10 is a cross sectional view showing a Y-Z section of an array transducer.

At step S108, a plurality of separating slits are formed in the assembly (the layered assembly 10 provided with the backing 51) which is formed at step S107, as shown in FIGS. 9 and 10. Here, FIG. 10 is a cross sectional view taken along the line A-A' of FIG. 9, in which the left-right direction corresponds to the Y direction and the upper-lower direction corresponds to the Z direction.

More specifically, a plurality of separating slits 46, 48 each having a width of W3 are formed at fixed intervals in the X direction so as to penetrate through the center parts of the corresponding reinforcing materials 38 from the top surface side. Each separating slit 46, 48 extends in the Y direction. Each separating slit 46 (the fifth slit) is formed corresponding to the first specified structure (the first face-to-face structure) 200U which is located toward the top surface, whereas each separating slit 48 (the sixth slit) is formed with regard to the second specified structure (the second face-to-face structure) 200D which is located toward the bottom surface. As will be detailed below, each specified structure is symmetrical with regard to the separating slit 46, 48. The width W3 of the separating slit 46, 48 is smaller than the width of the reinforcing material 38, and is 0.03 mm, for example. Further, the depth L3 of the separating slit 46, 48 is set such that the separating slit penetrates through at least the electrode member 60 of the backing 51, and is 0.6 mm, for example.

Referring now to FIG. 10, a plurality of separating slits 50 which are arranged in the Y direction 50 are also formed in the layered assembly 10. Each separating slit 50 extends in the X direction. The width and the depth of each separating slit 50 are the same as the width W3 and the depth L3 of the separating slit 46, 48. The plurality of separating slits 50 are formed before or after formation of the plurality of separating slits 46, 48. Alternatively, a plurality of separating slits 50 may be formed to have a width and a length which are different from those of the separating slits 46, 48. Even in this case, it is necessary to form the separating slits 50 by slicing to such a depth as to cut through at least the layered assembly 10 and the electrode member 60. Further, each separating slit 46, 48, 50 may be filled with an insulating material, an acoustic separating material, a reinforcing material or the like.

Referring back to FIG. 9, the backing 51 will be described. The backing 51 is made up mainly of a backing material 52, an electrode member 60 formed on the top surface of the backing material, and a plurality of signal lines 58 provided in a matrix form within the backing material 52. The plurality of signal lines 58 are disposed so as to correspond to the two dimensional arrangement of a plurality of transducer elements. Each signal line 58 is formed by a core material 56 which functions as an inner signal lead and a covering layer 54 surrounding the core material.

By forming a plurality of separating slits 46, 48 in the X direction in the layered assembly 10 and forming a plurality of separating slits 50 in the Y direction in the layered assembly 10 as described above, the layered assembly 10 is divided into a plurality of transducer elements. In such a state, the piezoelectric member 12 shown in FIG. 2 is divided into a plurality of piezoelectric layers 12A, and each of the piezoelectric members 14 and 16 is similarly divided into a plurality of piezoelectric layers 14A and 16A. Further, each of the inner electrode members 18, 20 is also divided into a plurality of inner electrode layers 18B and 20B. Also, the electrode member 60 of the backing 51 is similarly divided, as described above, to form a plurality of electrode pads 60A. Electrical connection between these layers will be described below with reference to FIG. 12.

Figure 11:
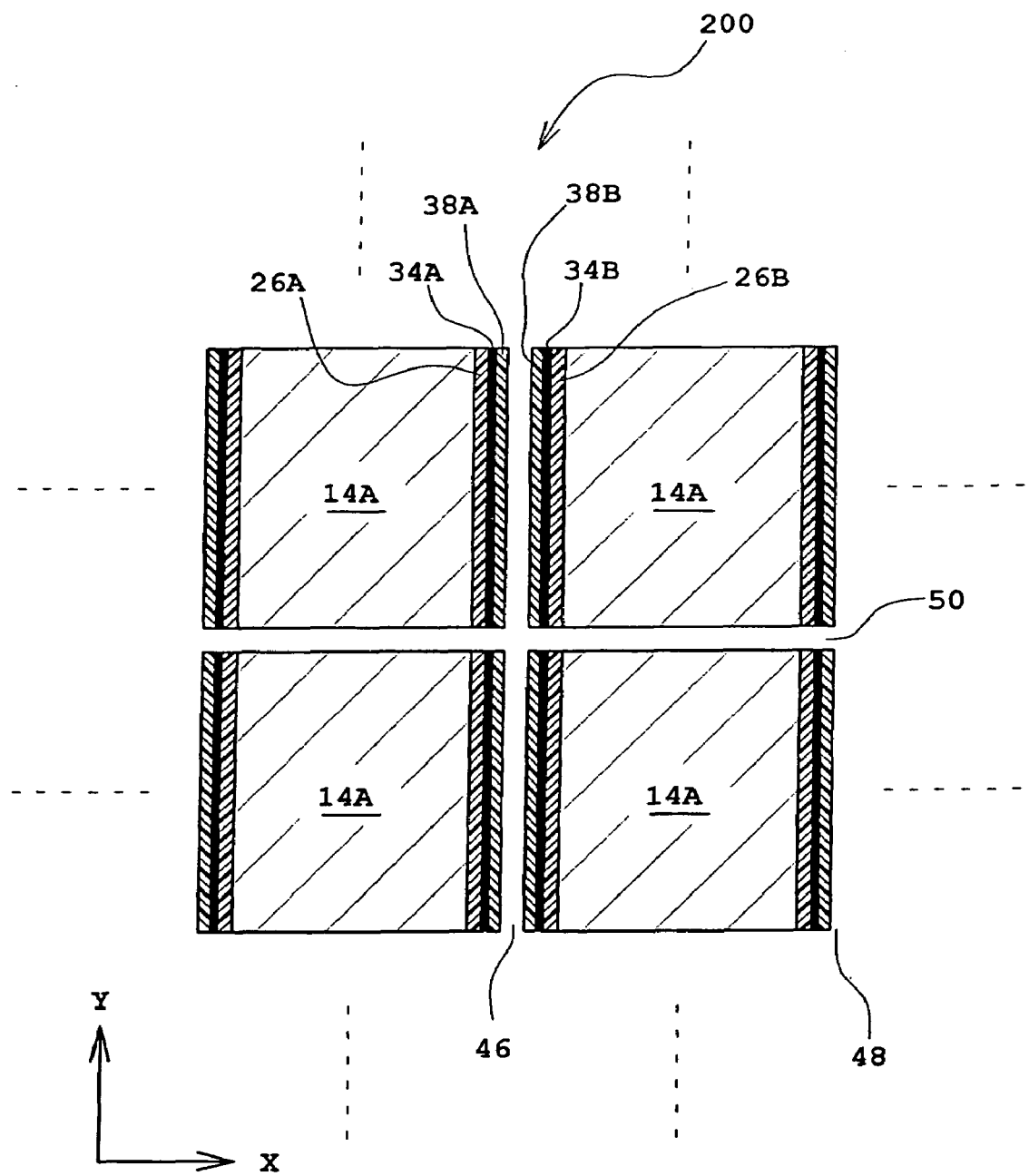
FIG. 11 is a cross sectional view taken along line B-B' of FIG. 9.

FIG. 11 is a cross sectional view taken along line B-B' of FIG. 9. As described above, with the formation of a plurality of separating slits 46 (or 48), for each pair of transducer elements adjacent to each other in the X direction (the left-right direction in the drawing), a specified structure 200 is formed across end parts of the two transducer elements forming each pair. The specified structure 200 includes a first specified structure 200U for ground and a second specified structure 200D for signal (see FIG. 9). These specified structures 200U, 200D are symmetrical to each other in the upper-lower direction. Further, each specified structure 200U, 200D is configured planar symmetrical with respect to a center plane (which is, more specifically, a virtual vertical plane centered in the separating slit 46, 48).

As shown in FIG. 11, the specified structure 200 includes a vertical electrode layer (side electrode layer) 34A formed on a transducer element on one side, a vertical electrode layer (side electrode layer) 34B formed on a transducer element on the other side, and a gap region formed between these vertical electrode layers 34A and 34B. More specifically, the specified structure 200 is formed by a vertical insulating layer 26A, the vertical electrode layer 34A, and a side reinforcing layer 38A, which are formed on a transducer element of one side, a vertical insulating layer 26B, the vertical electrode layer 34B, and a side reinforcing layer 38B, which are formed on a transducer element of the other side, and the separating slits 46, 48 provided between the side reinforcing layers 34A and 34B. In this example, the gap region is defined as a region formed by the side reinforcing layers 34A, 38A and the separating slits 46, 48. In another example described below, however, the gap region is defined as a region formed by a filler layer used for compounding, and the separating slit 46, 48.

At step S109 of FIG. 1, after formation of an array transducer which comprises a plurality of transducer elements as described above, a ground electrode member formed of a copper foil, for example, is provided on the top surface of the array transducer, and then a plurality of matching layers are further provided thereon in the two dimensional array. The assembly thus formed is disposed within a probe case which is not shown.

Figure 12:
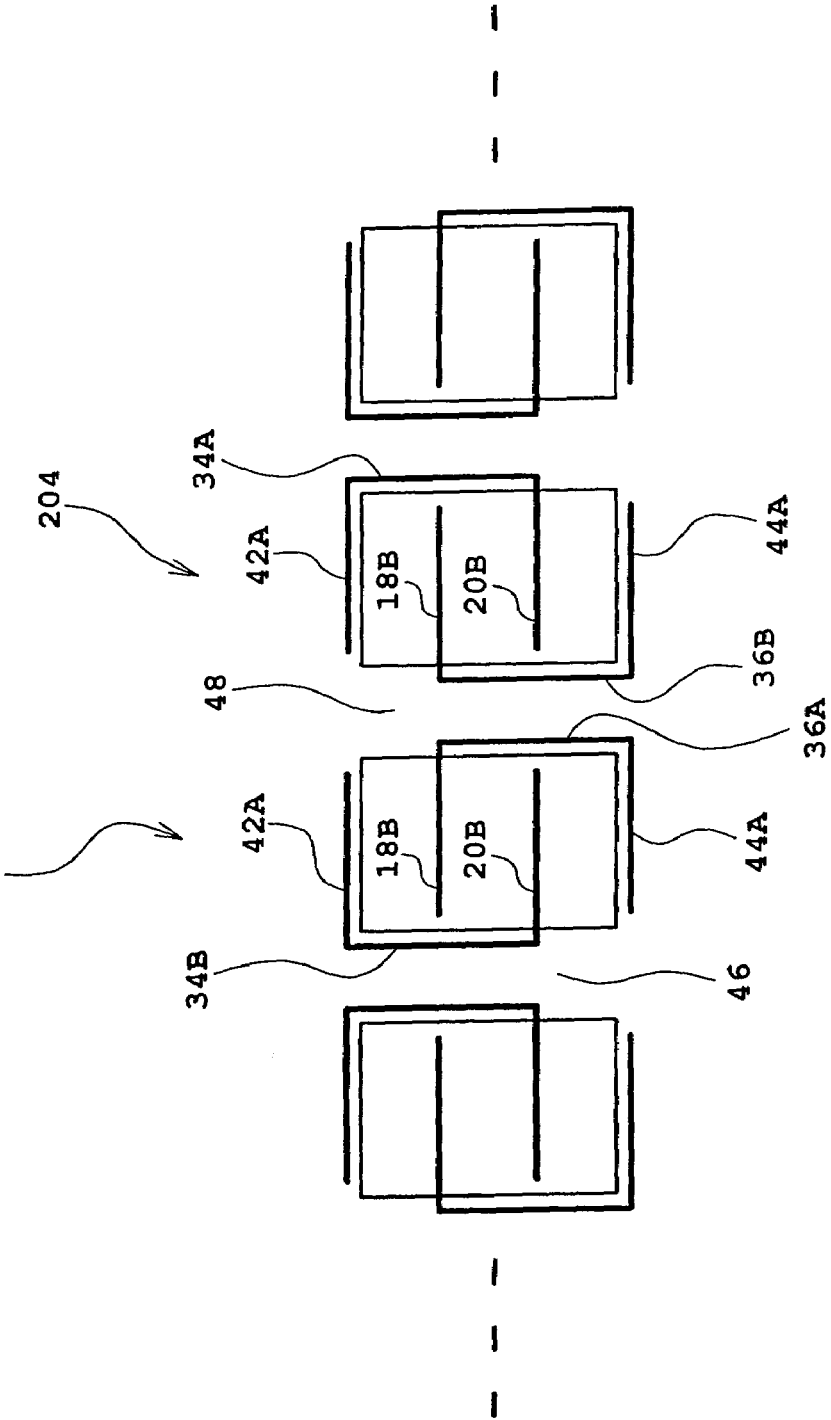
FIG. 12 is a schematic view for explaining an electrical connection in each transducer element.

FIG. 12 schematically shows an electrical connection relationship in the array transducer. When attention is paid to transducer elements 202 and 204, these transducer elements 202 and 204 are configured symmetrically to each other. With regard to the transducer element 202, the vertical electrode layer 34B is electrically connected to the top electrode layer 42A and the inner electrode layer 20B, which are the odd numbered layers counting from the top surface. Further, the vertical electrode layer 36A is electrically connected to the inner electrode layer 18B and the bottom electrode layer 44A, which are the even numbered layers counting from the top surface. Accordingly, by connecting the signal lead to the bottom electrode layer 44A and connecting the ground electrode member to the top surface electrode layer 42A, it is possible to cause the transducer element 202 to function as a so-called layered transducer element. Similarly, with regard to the transducer element 204, the vertical electrode layer 34A is electrically connected to the top electrode layer 42A and the inner electrode layer 20B, which are the odd numbered layers counting from the top surface. Further, the vertical electrode layer 36B is electrically connected to the inner electrode layer 18B and the bottom electrode layer 44A, which are the even numbered layers counting from the top surface.

Because the vertical electrode layer 36A of the transducer element 202 and the vertical electrode layer 36B of the transducer element 204 are in a symmetrical relationship, they can be fabricated easily. Further, although the vertical electrode layer 36A of the transducer element 202 and the vertical electrode layer 36B of the transducer element 204 face each other adjacently, it is advantageous in terms of insulation property because they have the same polarity.

In the ultrasonic probe according to the above embodiment, due to the use of a layered transducer element, electrical impedance can be reduced. Further, use of the vertical electrode layers reduces or eliminates a problem of loss of oscillation area in a transducer element or reduction of oscillation efficiency. In other words, sensitivity of the ultrasonic probe can be increased. Further, according to the above-described manufacturing process, two types of specified structures are provided alternately, so that electrical connection between the layered transducer elements can be reliably achieved. Also, because the two vertical electrode layers facing each other have the same polarity, the withstand voltage level between the signal line and the ground line can be increased.

Several other example processes of manufacturing an ultrasonic probe will be described. Each example manufacturing process described below is similar to the above-described manufacturing process in that it includes a step of creating a plurality of specified structures and is different from the above-described process in that it includes a step of performing compounding of the layered assembly. In each example, similar elements are denoted by the same or similar numerals.

First, with reference to FIGS. 13 to 20, the second example process of manufacturing an ultrasonic probe will be described. This example is characterized by performing compounding of the layered assembly (i.e. composite laminated assembly) in the first place.

Figure 13:
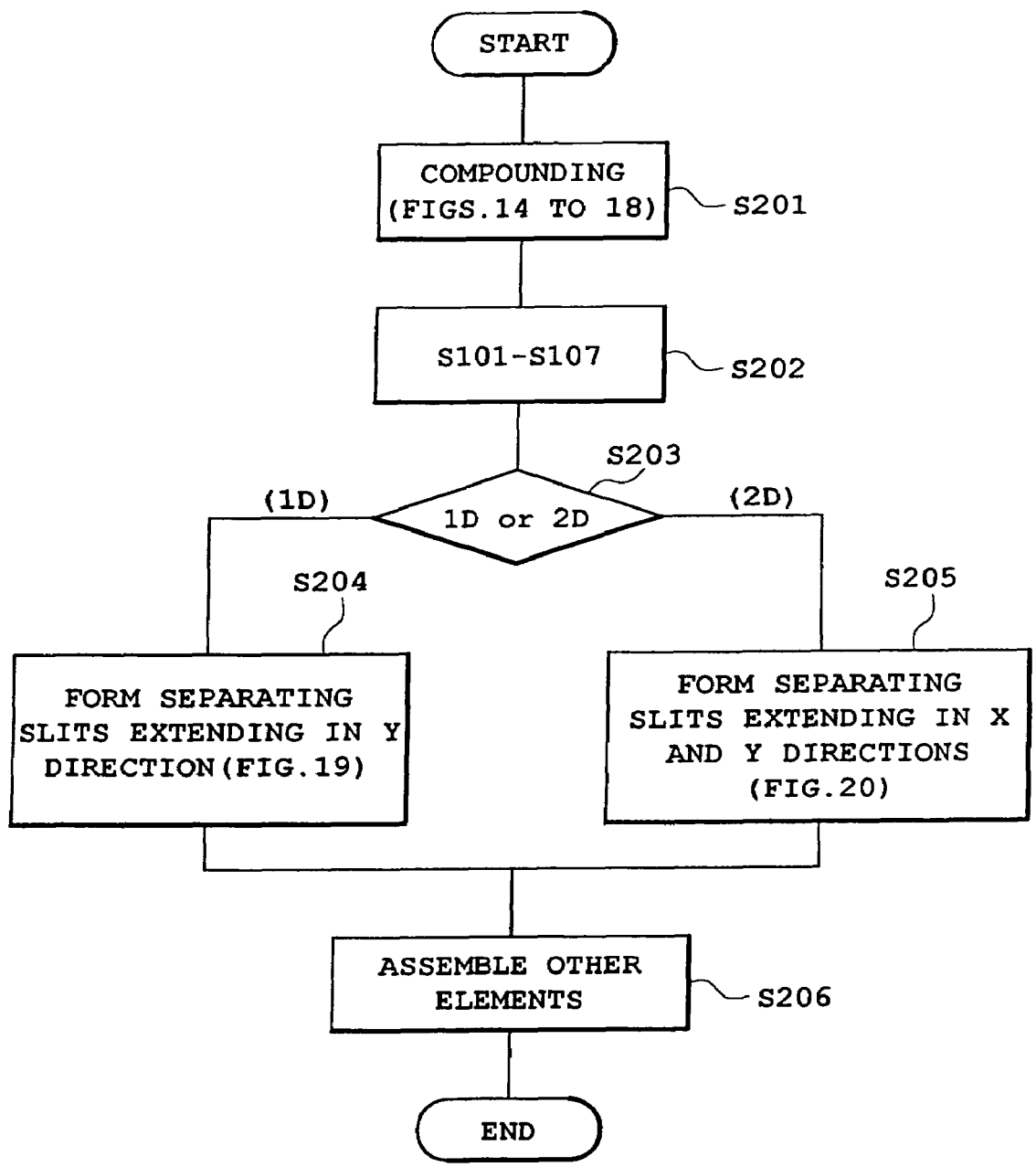
FIG. 13 a flow chart for explaining a second example process of manufacturing an ultrasonic probe according to the present invention.
Figure 14:
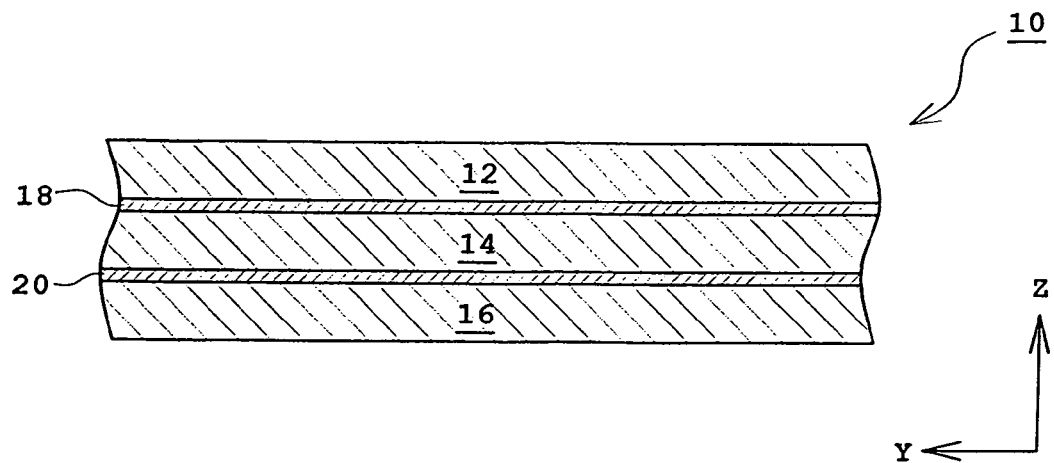
FIG. 14 is a cross sectional view showing a layered assembly.
Figure 15:
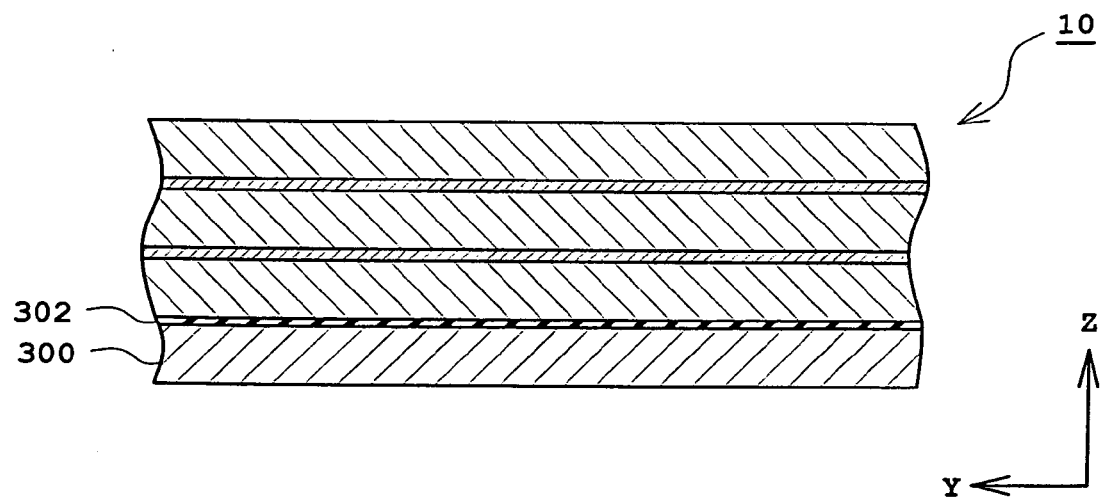
FIG. 15 is a cross sectional view showing a layered assembly to which a base member is temporarily bonded.
Figure 16:
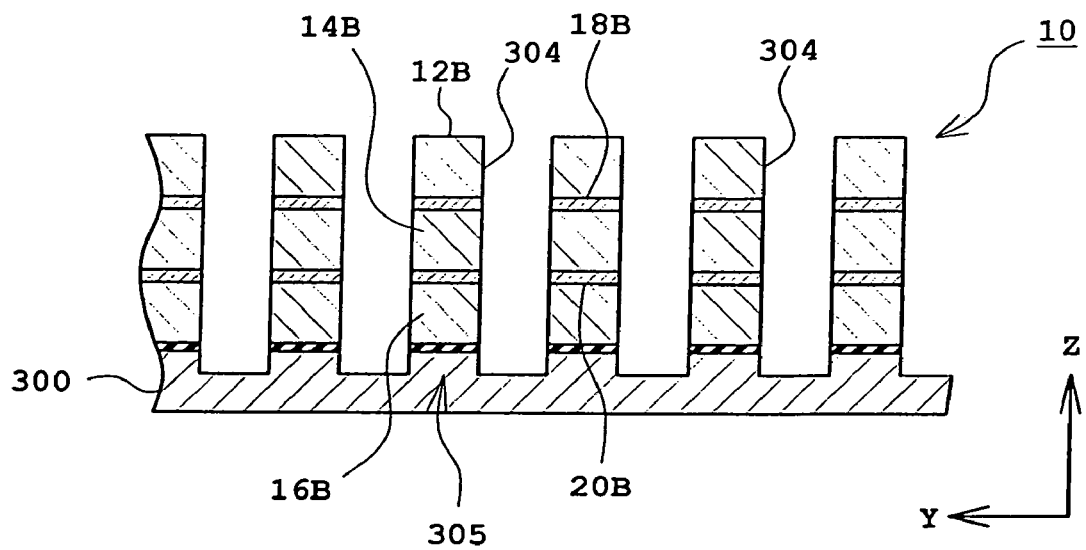
FIG. 16 is a cross sectional view showing a layered assembly in which a plurality of compounding slits are formed.
Figure 17:
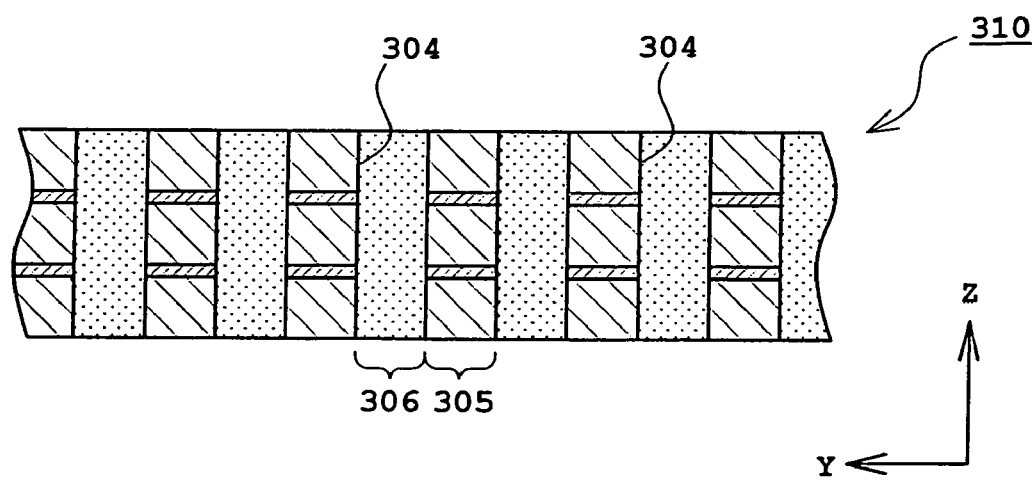
FIG. 17 is a cross sectional view showing a layered assembly after filling of a resin material.
Figure 18:
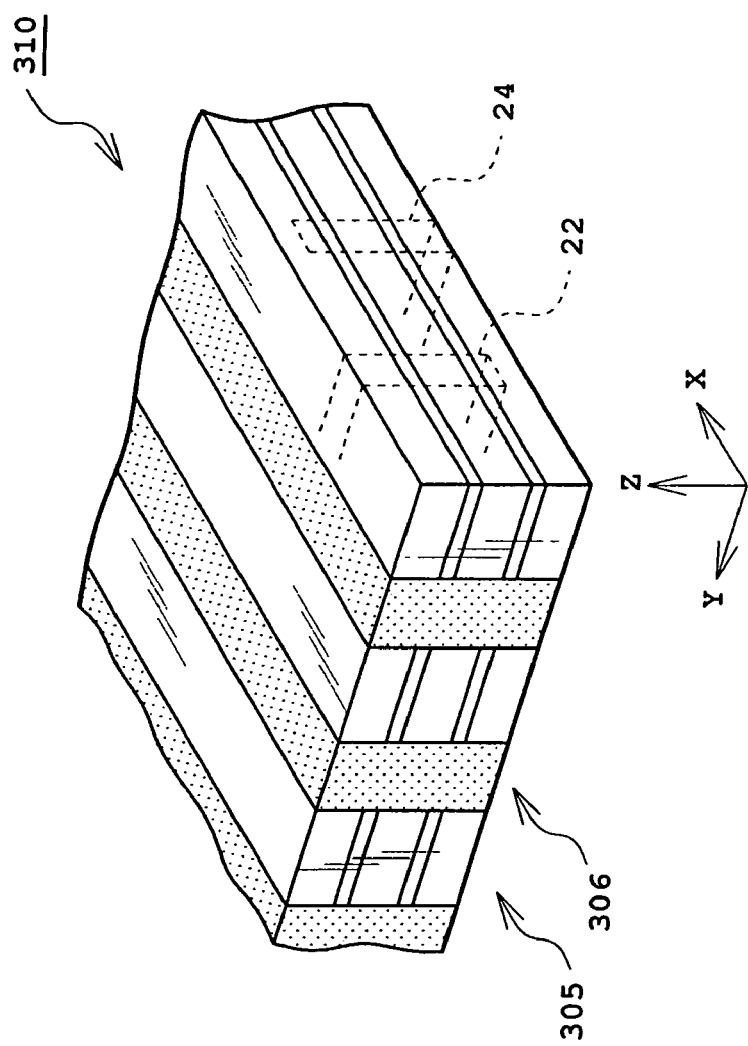
FIG. 18 is a perspective view of a layered assembly which is compounded in the Y direction.

FIG. 13 shows the manufacturing process in the form of a flow chart. At step S201, compounding is performed for a layered assembly, as will be described specifically. Referring to FIG. 14, a layered assembly which is the same as the layered assembly 10 in FIG. 2 is shown in a cross sectional view taken in a different direction from that of FIG. 2. Referring to FIG. 15, a base member 300 is bonded to the bottom surface of the layered assembly 10 using an adhesive material 302. Then, as shown in FIG. 16, a plurality of slits 304 used for compounding are formed in the layered assembly 10 through the top surface at fixed intervals in the Y direction. The depth of the slit 304 is set such that the slit penetrates through the entire thickness of the layered assembly 10 to slightly cut into the base member 300. With the formation of a plurality of slits 304, each of the piezoelectric members 12, 14, 16 is divided into a plurality of elements 12B, 14B, 16B, and each of the inner electrode members 18, 20 is also divided into a plurality of elements 18B, 20B. At this stage, a plurality of piezoelectric sections 305 are formed. Each piezoelectric section is made up of the elements 12B, 14B, 16B, 18B, and 20B which are layered in the vertical direction. The base member 300 prevents a plurality of piezoelectric sections 305 from being separated into pieces. Then, the plurality of slits 304 are filled with a resin material as a filler material, and the layered assembly 10 is heated to harden the resin material. As a result, a plurality of resin layers (resin sections) 306 are formed. The resin material is a material used for compounding which includes an epoxy resin and a silicone resin as a main component. After the plurality of resin layers 306 are formed, the base member 300 is removed from the layered assembly 10. FIG. 17 shows the layered assembly in this state as a cross sectional view, in which the composite layered assembly is denoted by numeral 310. FIG. 18 is a perspective view showing the layered assembly 310, in which a plurality of base slits 22, 24 which will be formed later are shown by dotted line.

At step S202 of FIG. 13, steps S101 to S107 in FIG. 1 are performed. Then, when a 1D array transducer is to be formed from the layered assembly 310, step S204 is performed after S203, whereas when a 2D array transducer is to be formed from the layered assembly 310, step S205 is performed after step S203.

Figure 19:
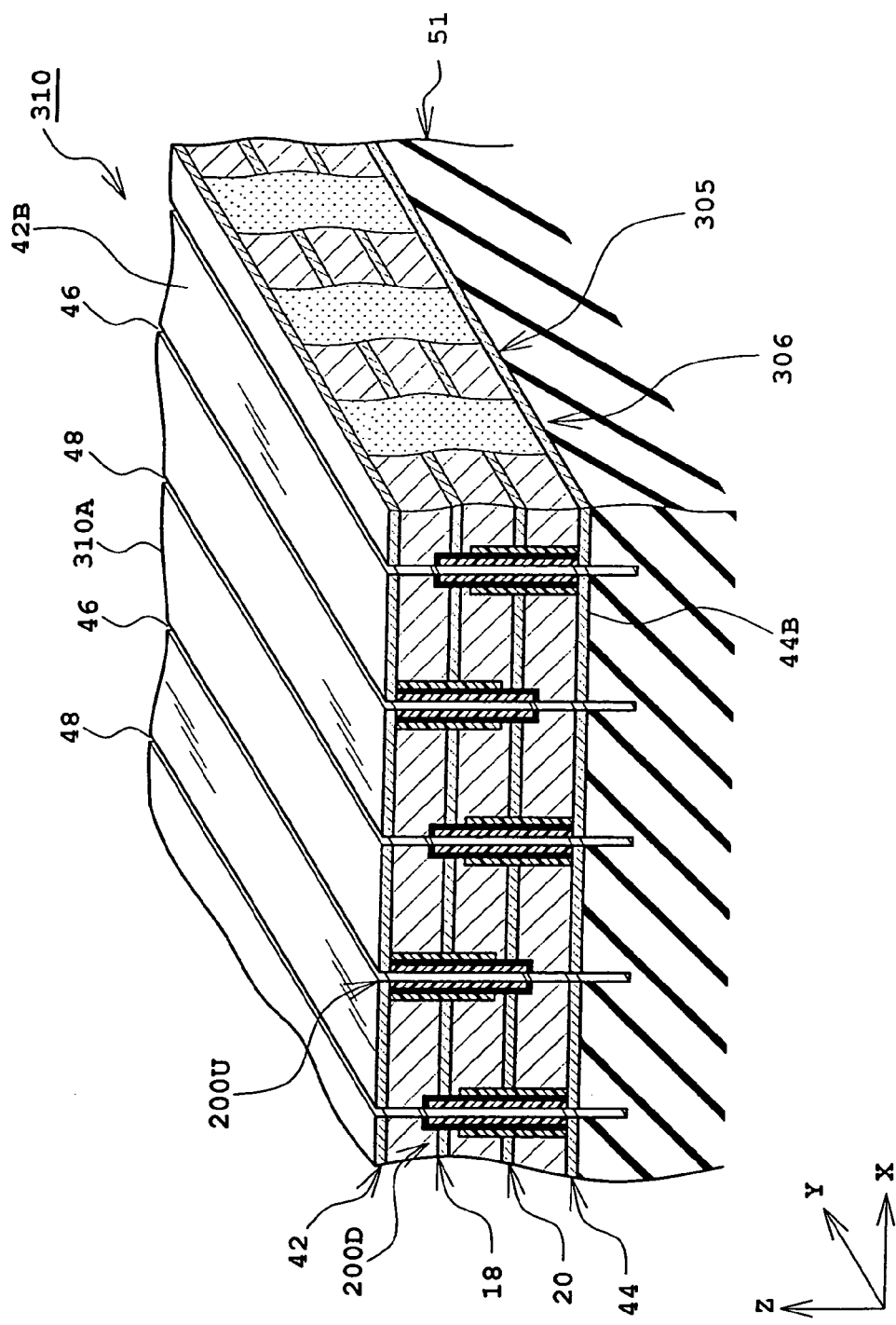
FIG. 19 is a perspective view of a layered 1D array transducer which is compounded in the Y direction.

At step S204, a plurality of separating slits 46, 48 are formed in the layered assembly 310 in the X direction, as shown in FIG. 19. Each separating slit 46, 48 extends in the Y direction. Each separating slit 46 is formed at the center of each specified structure (the specified structure for ground) 200U, and each separating slit 48 is formed at the center of each specified structure (the specified structure for signal) 200D. In the layered assembly 310 shown in FIG. 19, a plurality of piezoelectric sections 305 and a plurality of resin sections 306 are arranged alternately in the Y direction and a plurality of transducer elements 310A are arranged in the X direction. For each pair of adjacent transducer elements, the specified structure 200U or 200D is created across these transducer elements. Thus, a 1D array transducer is formed in which an array direction corresponds to the X direction and which is compounded in the Y direction.

Figure 20:
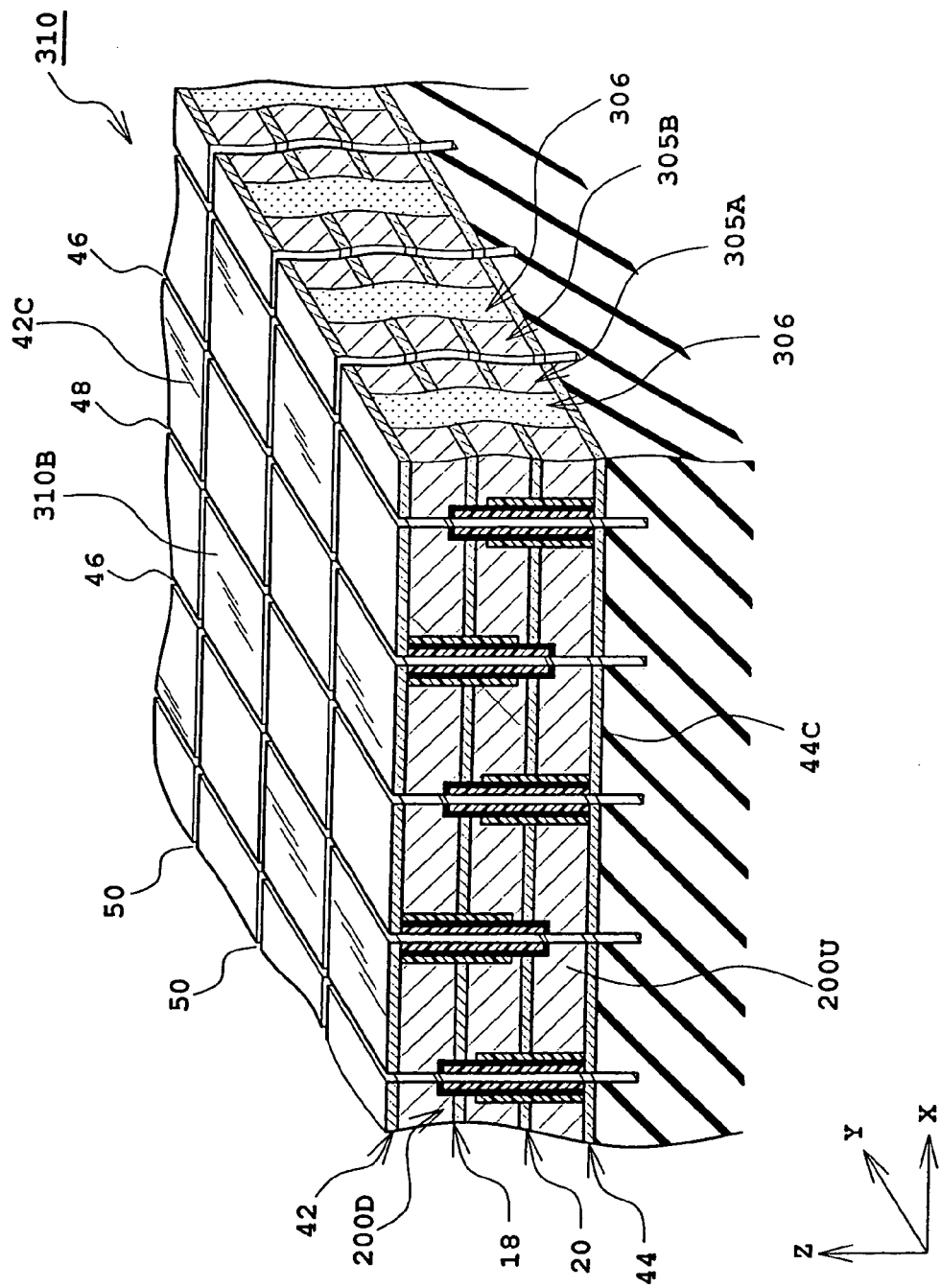
FIG. 20 is a perspective view of a layered 2D array transducer which is compounded in the Y direction.

On the other hand, at step S205, a plurality of separating slits 46 and 48 are formed in the X direction and a plurality of separating slits 50 are formed in the Y direction in the layered assembly 310, as shown in FIG. 20. Each separating slit 46, 48 extends in the Y direction and each separating slit 50 extends in the X direction. With the formation of these separating slits 46, 48, and 50, a plurality of transducer elements 310B are formed in a two dimensional array. More specifically, each separating slit 46 is formed at the center of each specified structure (the specified structure for ground) 200U, and each separating slit 48 is formed at the center of each specified structure (the specified structure for signal) 200D. Each separating slit 50 is formed so as to divide either one of the piezoelectric section 305 and the resin section 306 into two parts, or is formed along the border of the piezoelectric section 305 and the resin section 306. In the example shown in FIG. 20, the (whole) piezoelectric section 305 is divided into two parts by each separating slit 50, thereby forming a piezoelectric section (one side half) 305A included in a transducer element on one side in the Y direction and a piezoelectric section (the other side half) 305B included in a transducer element on the other side in the Y direction. Thus, a 2D array transducer which is compounded in the Y direction is formed.

At step S206 of FIG. 13, other elements are provided to the layered assembly 310, similar to the step S109 of FIG. 1. Further, the number, size, and pitch of the piezoelectric sections and the resin sections in the Y direction can be determined as desired. For example, more piezoelectric sections and resin sections may be provided for one transducer element. The electrode member 60 and a plurality of signal lines 58 shown in FIG. 9 and so on are omitted in FIGS. 19 and 20, and are omitted also in FIGS. 22, 23, 31, 32, 34 and 35 which will be described below.

Figure 21:
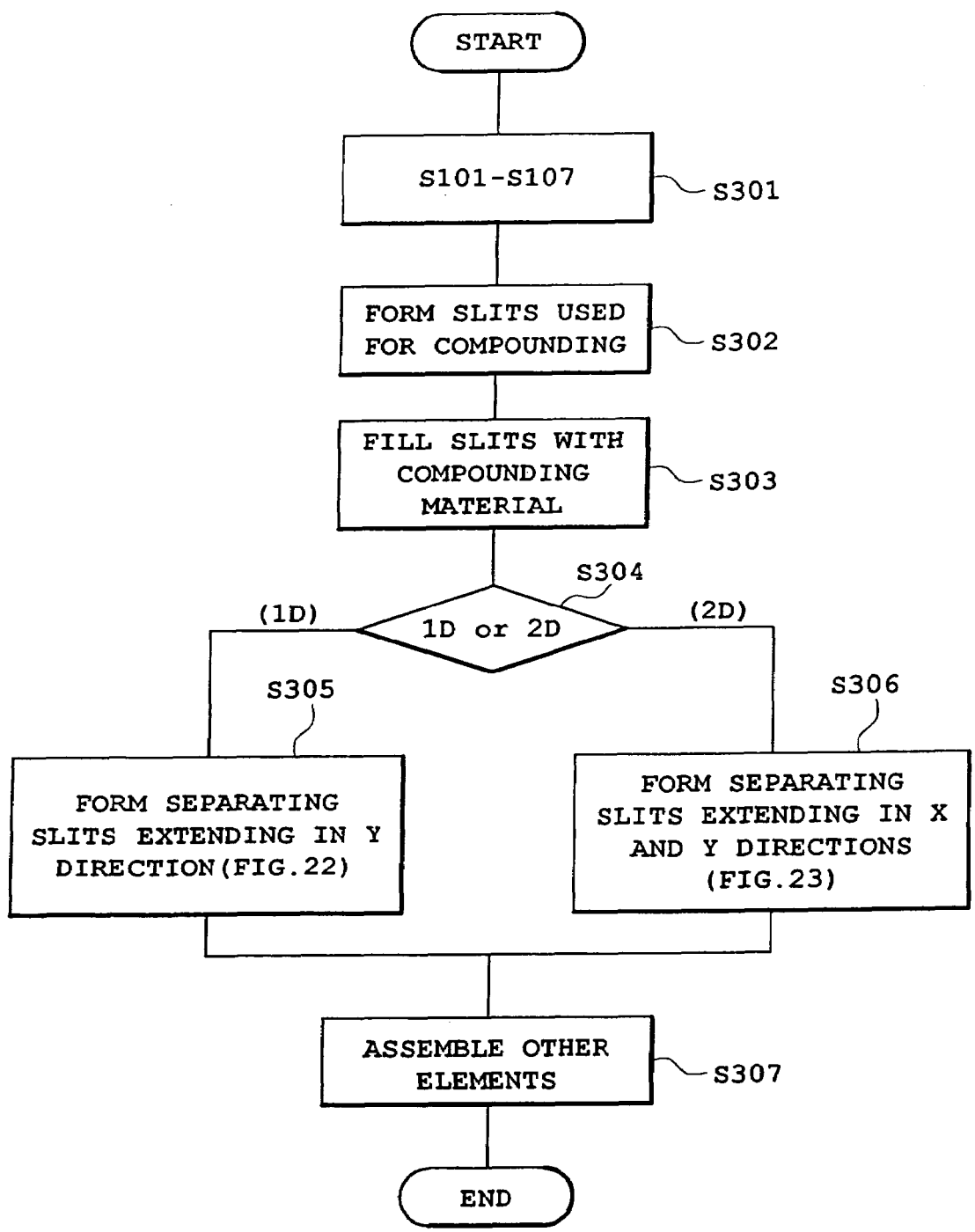
FIG. 21 a flow chart for explaining a third example process of manufacturing an ultrasonic probe according to the present invention.
Figure 22:
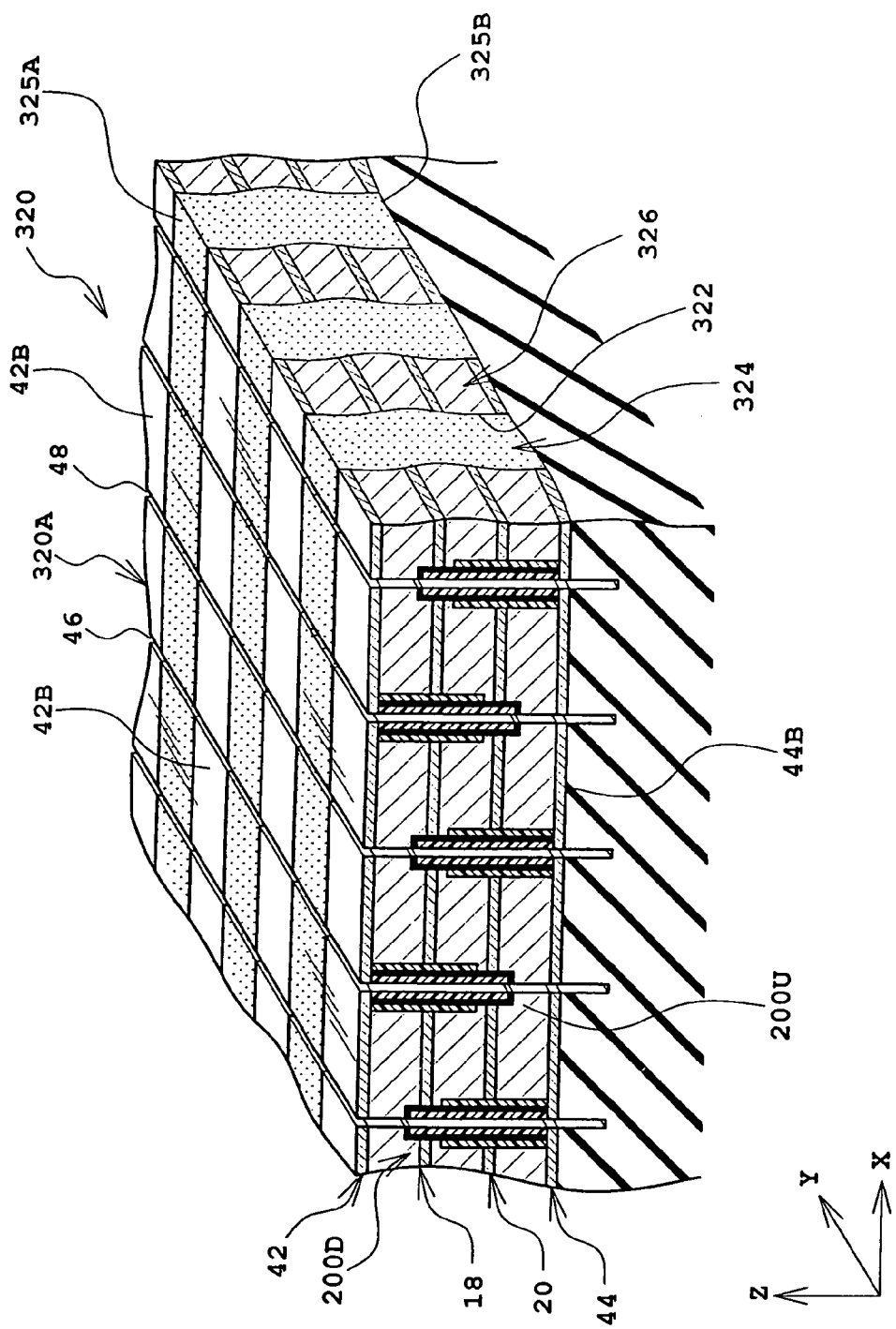
FIG. 22 is a perspective view showing a layered 1D array transducer fabricated by performing compounding in the Y direction with regard to a layered assembly after formation of a top electrode member and a bottom electrode member.
Figure 23:
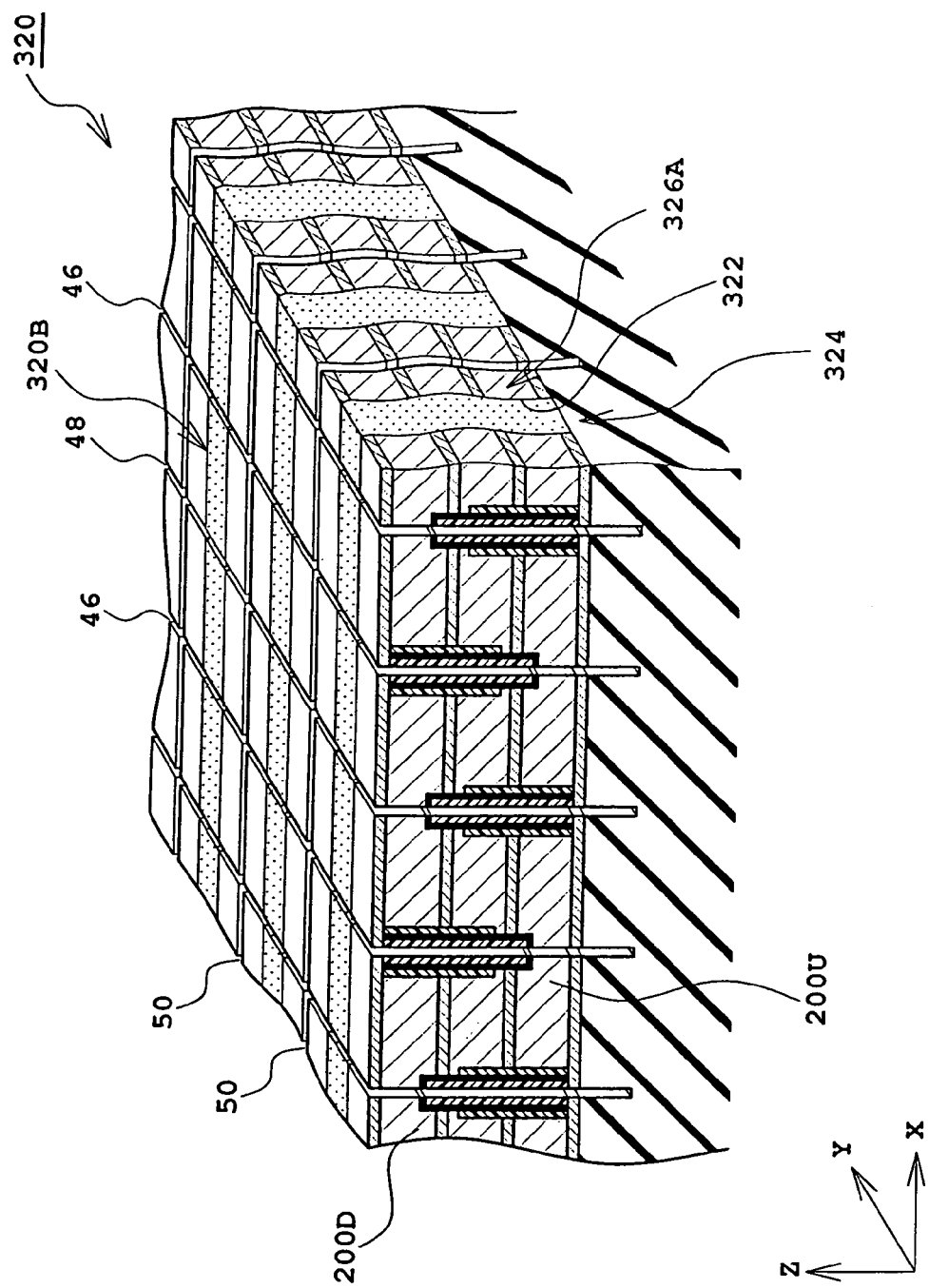
FIG. 23 is a perspective view showing a layered 2D array transducer fabricated by performing compounding in the Y direction with regard to a layered assembly after formation of a top electrode member and a bottom electrode member.

Referring now to FIGS. 21 to 23, the third example process of manufacturing an ultrasonic probe will be described. This example is characterized by performing compounding of the layered assembly after formation of the specified structures.

FIG. 21 shows the manufacturing process in the form of flow chart. At step S301, steps S101 to S107 shown in FIG. 1 are performed. At step S302, a plurality of specified structures, a top electrode member, and bottom electrode member are formed. Also, a plurality of slits used for compounding (hereinafter referred to as compounding slits) are formed in the Y direction in a layered assembly to which a backing is bonded. Each compounding slit extends in the X direction. At step S303, these compounding slits are filled with a resin material used for compounding, which is then hardened by heating.

When a 1D array transducer is to be formed, step S305 is performed after step S304. At step S305, a plurality of separating slits 46, 48 are formed in the X direction, as shown in FIG. 22. Each separating slit 46, 48 extends in the Y direction. With the formation of the separating slits 46 and 48, a plurality of transducer elements 320A arranged in the X direction are formed. Each transducer element 320A is made up of a plurality of piezoelectric sections 326 and a plurality of resin sections 324 which are arranged alternately in the Y direction. As described above, each resin section 324 is formed by filling the compounding slit 322 with a resin material. Because a plurality of slits 322 are formed after formation of the top electrode member 42 and the bottom electrode member 44, each of the top electrode member 42 and the bottom electrode member 44 is also divided into a plurality of electrode layers by the plurality of slits 322. (FIG. 22 shows a plurality of top electrode layers 42B.) Consequently, the top electrode layer and the bottom electrode layer are not provided on the top surface 325A and the bottom surface 325B of each resin layer (resin section) 324, respectively.

On the other hand, when a 2D array transducer is to be formed after step S303, step S306 is performed after step S304. At step S306, a plurality of separating slits 46, 48 are formed in the X direction and a plurality of separating slits 50 are formed in the Y direction, as shown in FIG. 23. Each separating slit 46, 48 extends in the Y direction, and each separating slit 50 extends in the X direction. With the formation of these slits, a plurality of transducer elements 320B arranged in a two dimensional array in the X and Y directions are formed. Each transducer element 320B is made up of at least one piezoelectric section 326 and at least one resin section 324 alternately arranged in the Y direction. As described above, each resin section 324 is formed by filling the compounding slit 322 with a resin material. Each separating slit 50 is formed at such a position as to divide any piezoelectric section or any resin section into two parts, or is formed at the border between any piezoelectric section and any resin section. In the example shown in FIG. 23, each piezoelectric section is divided into two parts by each separating slit 50, so that two piezoelectric sections 326A are formed. As in the example shown in FIG. 22, a plurality of slits 322 are formed after formation of the top electrode member 42 and the bottom electrode member 44. At step S307 of FIG. 21, other members are bonded to the plurality of transducer elements shown in FIGS. 22 and 23.

Next, with reference to FIGS. 24 to 32, the fourth example process of manufacturing an ultrasonic probe will be described. This example is characterized by the fact that compounding in the X direction in a layered assembly is performed simultaneously with formation of a plurality of specified structures.

Figure 24:
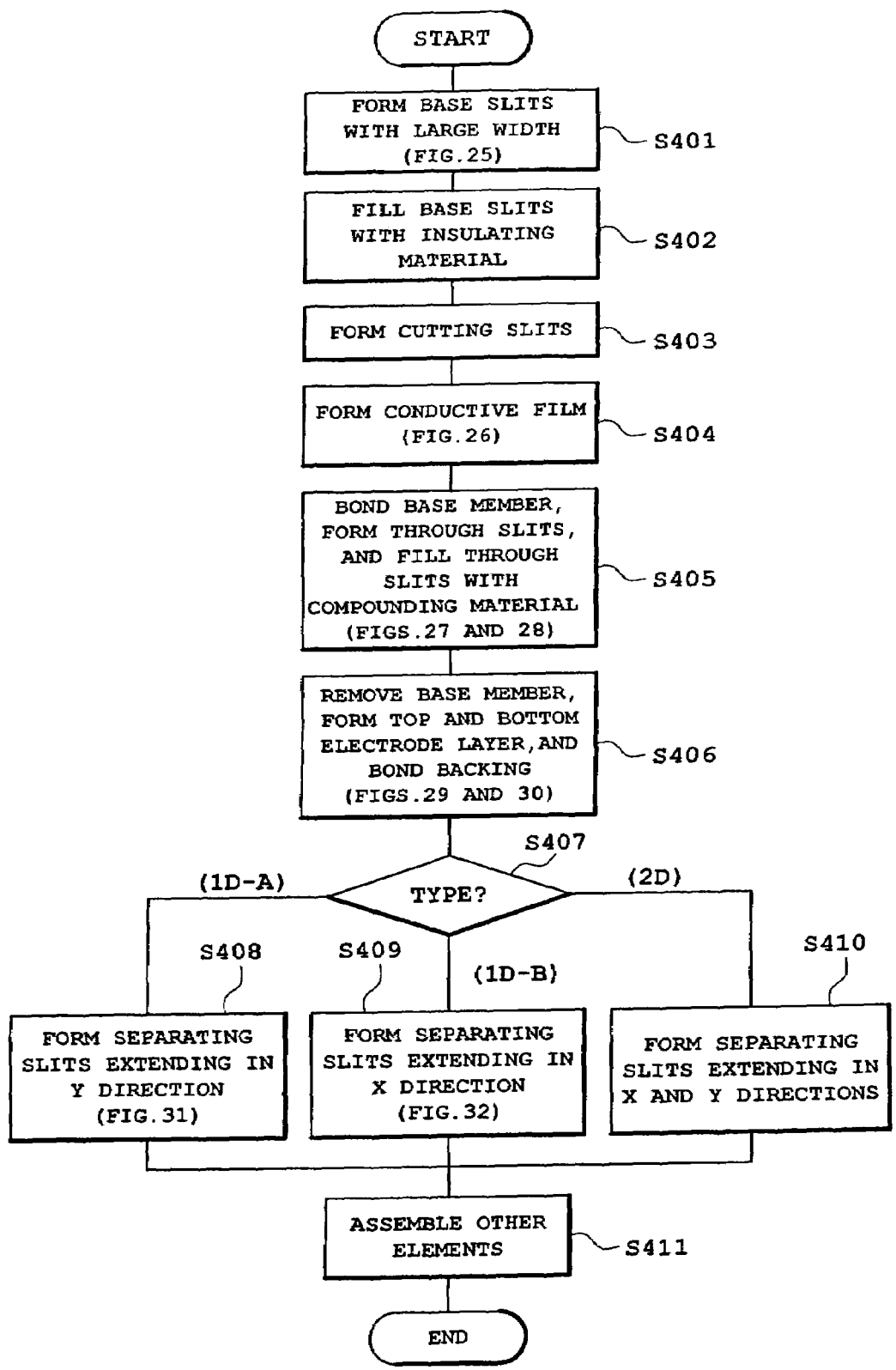
FIG. 24 is a flow chart for explaining a fourth example process of manufacturing an ultrasonic probe according to the present invention.
Figure 25:
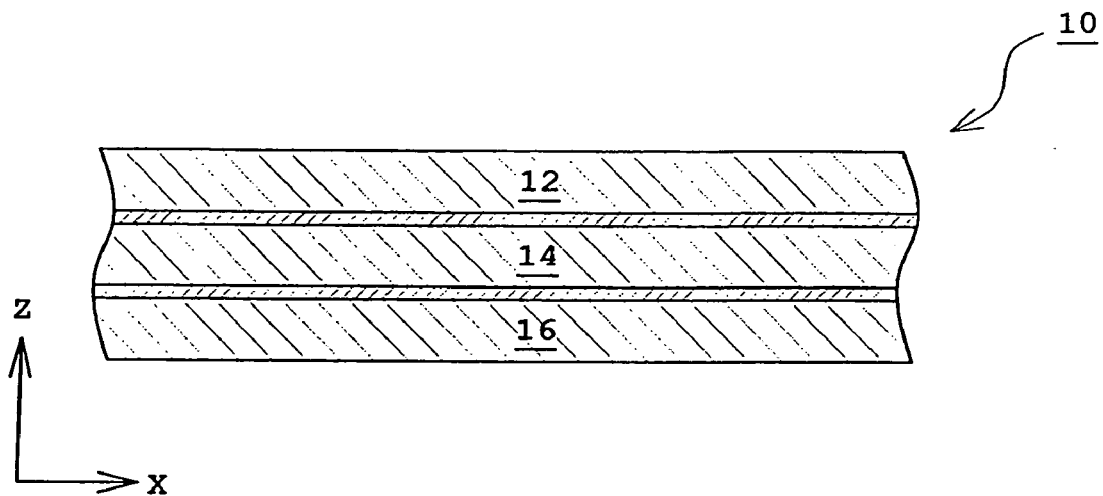
FIG. 25 is a cross sectional view showing a layered assembly.

FIG. 24 shows the manufacturing process in the form of flow chart. At step S401, as in step S101 of FIG. 1, a plurality of base slits are formed in a layered assembly. More specifically, as shown in FIG. 25, a plurality of base slits having a large width are formed at fixed intervals in the X direction through the top surface of the layered assembly 10 (which is the same as the layered assembly 10 shown in FIG. 2), and a plurality of base slits having a large width are formed at fixed intervals in the X direction through the bottom surface of a layered assembly 10. The width of these base slits are set to a size which is necessary for compounding, and is greater than the normal width as shown in FIG. 3.

Figure 26:
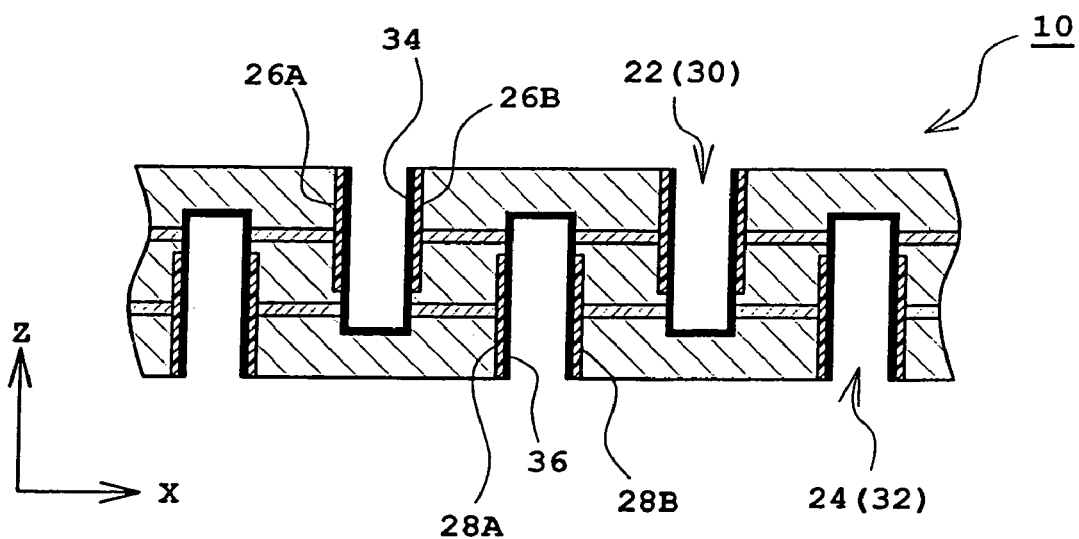
FIG. 26 is a cross sectional view showing a layered assembly in which base slits, an insulating material and conductive films are provided.

Then, at step S402, as in step S102, each base silt is filled with an insulating material, which is then hardened. At step S403, as in step S103, a plurality of cutting slits are formed, so that a pair of vertical insulating layers are formed within each base slit, as shown in FIG. 26. As shown in FIG. 26, a conductive film 34, 36 is then formed on the inner surface of vertical insulating layers 26A and 26B.

Figure 27:
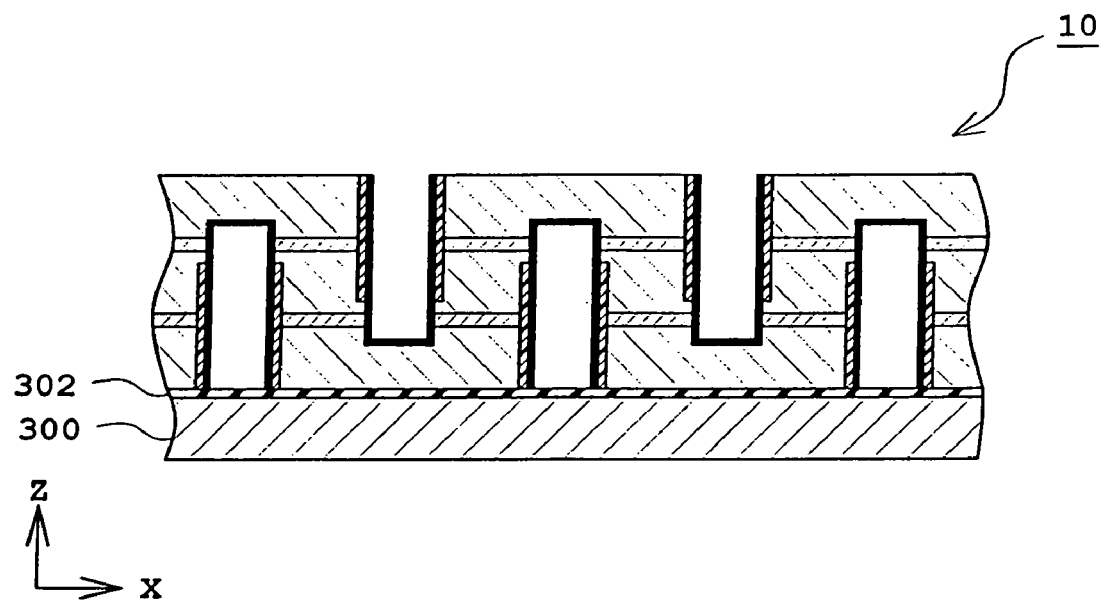
FIG. 27 is a cross sectional view showing a layered assembly to which a base member is temporarily bonded.
Figure 28:
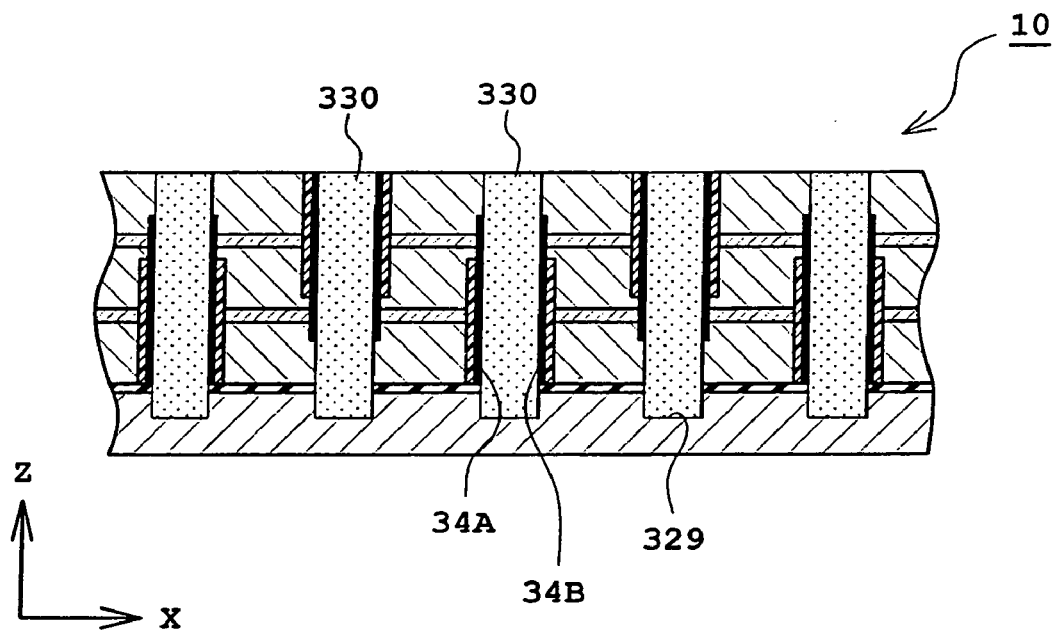
FIG. 28 is a cross sectional view showing a layered assembly in which slits are filled with a resin material used for compounding.
Figure 29:
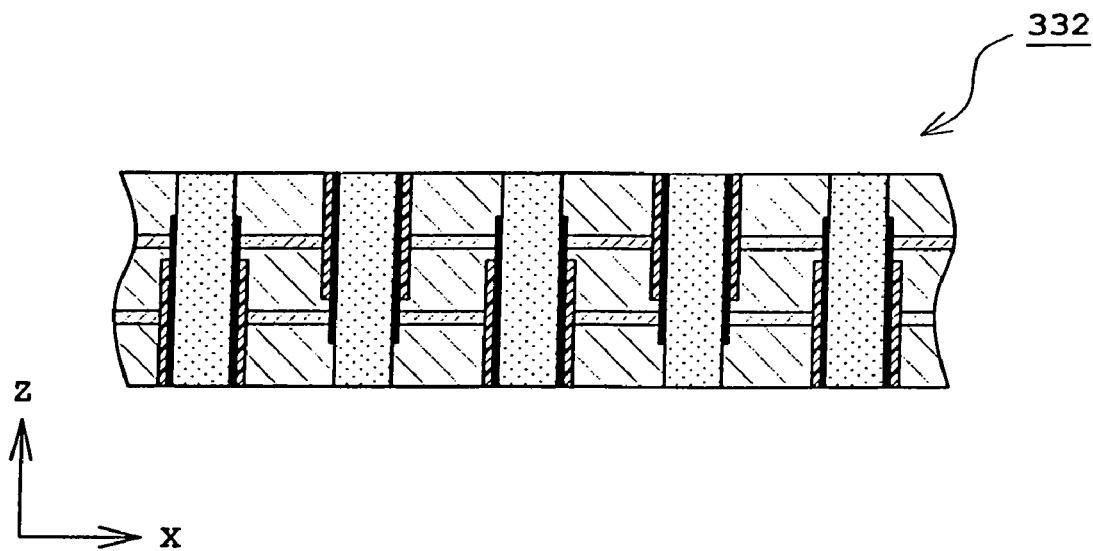
FIG. 29 is a cross sectional view showing a layered assembly from which a base member is removed.
Figure 30:
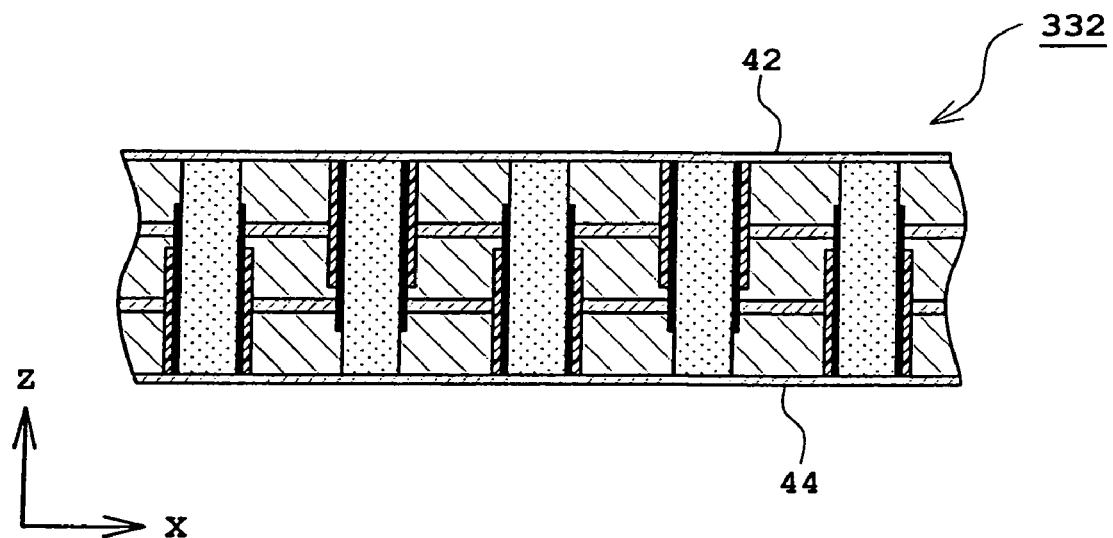
FIG. 30 is a cross sectional view showing a layered assembly on which a top electrode member and a bottom electrode member are provided.

At step S405 of FIG. 24, as shown in FIG. 27, a base member 300 is first bonded on the bottom surface of the layered assembly 10 using an adhesive material 302. Then, a process of forming each cutting slit 30, 32 into a through slit which penetrates through the entire depth of the layered assembly 10 is performed. More specifically, with regard to each cutting slit 30, the third piezoelectric member 16 from the top is cut entirely in the Z direction, whereas with regard to each cutting slit 32, the uppermost piezoelectric member 12 is cut entirely in the Z direction. As a result, a plurality of compounding slits 329 are formed in the layered assembly, as shown in FIG. 28. Further, at step S405, these compounding slits 329 are filled with a resin material 330 used for compounding, which is then hardened by heating. The resin material 330 constitutes a resin layer or a resin section.

At step S406 of FIG. 24, the base member 300 is removed from the layered assembly 10, so that a layered assembly 332 which is compounded (namely, a compound layered assembly) is obtained. Then, a top electrode member 42 and a bottom electrode member 44 are formed on the layered assembly 332. Further, a backing is bonded to the bottom electrode member 44.

Figure 31:
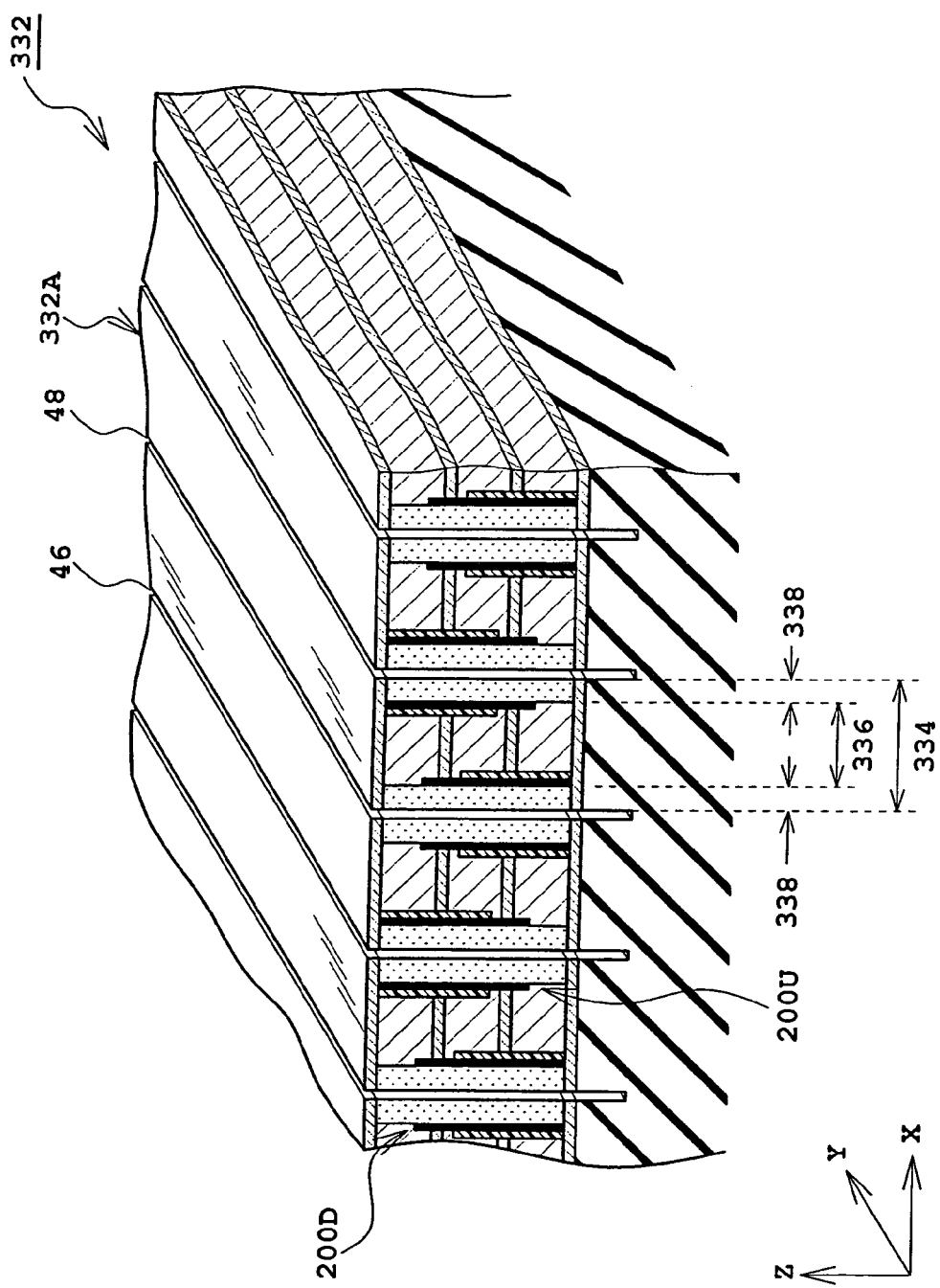
FIG. 31 is a view showing a layered 1D array transducer which is compounded in the X direction and separated in the X direction.

When a 1D array transducer (type A) is to be formed, step S408 is performed after step S407. At step S408, a plurality of separating slits 46, 48 are formed in the X direction so as to correspond to the respective center positions of a plurality of specified structures. Thus, a 1D array transducer in which a plurality of transducer elements 332A are arranged in the X direction is formed, as shown in FIG. 31. Referring to FIG. 31, numeral 334 corresponds to one transducer element 332A, and numeral 336 denotes a piezoelectric section, while numeral 338 denotes a pair of resin sections formed on both sides of the piezoelectric section 336. Thus, each transducer element 332A is compounded in the X direction.

Figure 32:
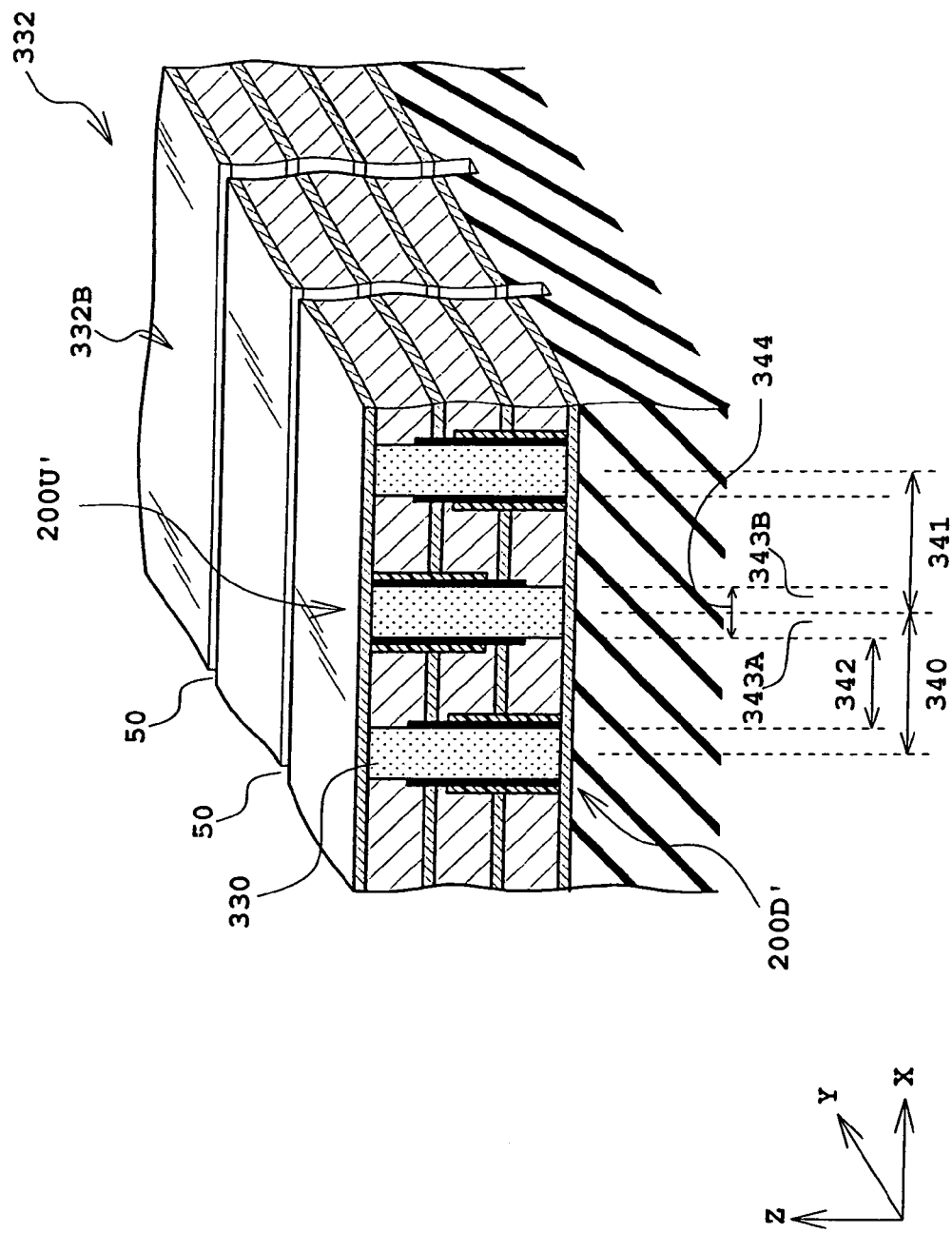
FIG. 32 is a view showing a layered 2D array transducer which is compounded in the x direction and separated in the Y direction.

When a 1D array transducer (type B) is to be formed, on the other hand, step S409 is performed after step S407. At step S409, a plurality of separating slits 50 are formed in the Y direction. Each separating slit 50 extends in the X direction. Consequently, a 1D array transducer in which a plurality of transducer elements 332B are arranged in the Y direction as shown in FIG. 32 is formed. Each transducer element 332B has its longitudinal direction corresponding to the X direction and is compounded in this direction. Referring to FIG. 32, when seen from one point of view, each transducer element 332B is a member formed by coupling a plurality of elements (corresponding to segments) 340, 341. The specified structure 200U' or 200D' is formed across the two adjacent segments 340 and 341, and the specified structure 200U' or 200D' includes the resin layer (resin section) 344 in the middle part. While the resin layer 344 has no separating slit in the example shown in FIG. 32, the resin layer 344 is conceptually divided into a section 343A included in the segment 340 on one side and a section 343B included in the segment 341 on the other side. When seen from another point of view, each transducer element 332B is a member formed by coupling a plurality of piezoelectric sections 342 and a plurality of resin sections 344 which are provided alternately in the X direction.

On the other hand, when a 2D array transducer is to be formed, step S410 is performed after step s407. At step S410, a plurality of separating slits are formed in the X direction at positions corresponding to the respective center positions of a plurality of specified structures, and a plurality of separating slits are formed in the Y direction. As a result, the layered assembly compound in the X direction is divided into a plurality of transducer elements arranged in the X and Y directions. In other words, a plurality of separating slits (corresponding to the plurality of the separating slits 50 shown in FIG. 10) are formed on the layered assembly 332 shown in FIG. 31 in Y direction, thereby forming a plurality of transducer elements. Then, at step S411 of FIG. 24, other processes such as formation of a matching layer are performed.

Next, referring to FIGS. 33 to 35, the fifth example process of manufacturing an ultrasonic probe will be described. This example is characterized by compounding of a layered assembly in the X and Y directions.

Figure 33:
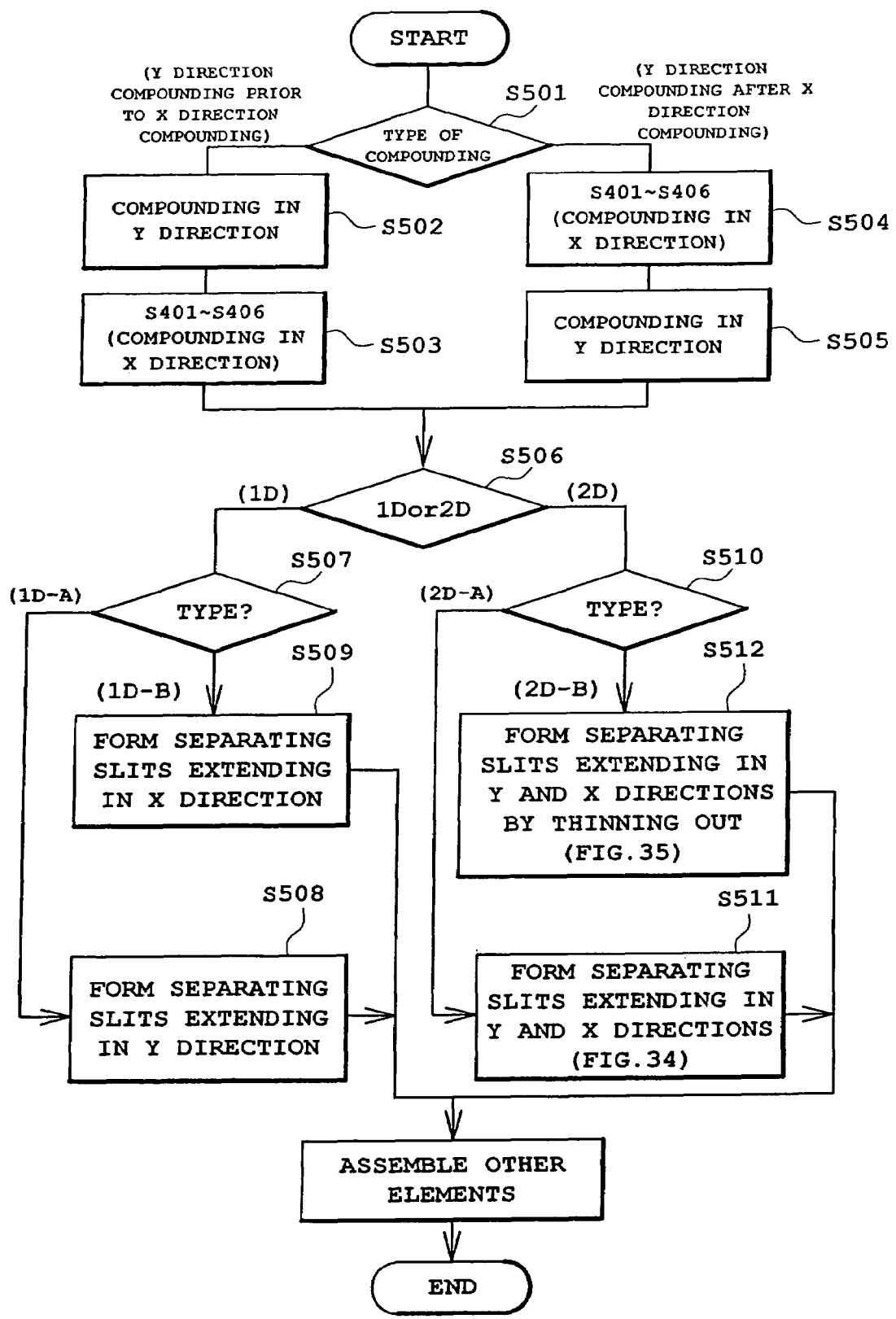
FIG. 33 is a flow chart for explaining a fifth example process of manufacturing an ultrasonic probe according to the present invention.
Figure 34:
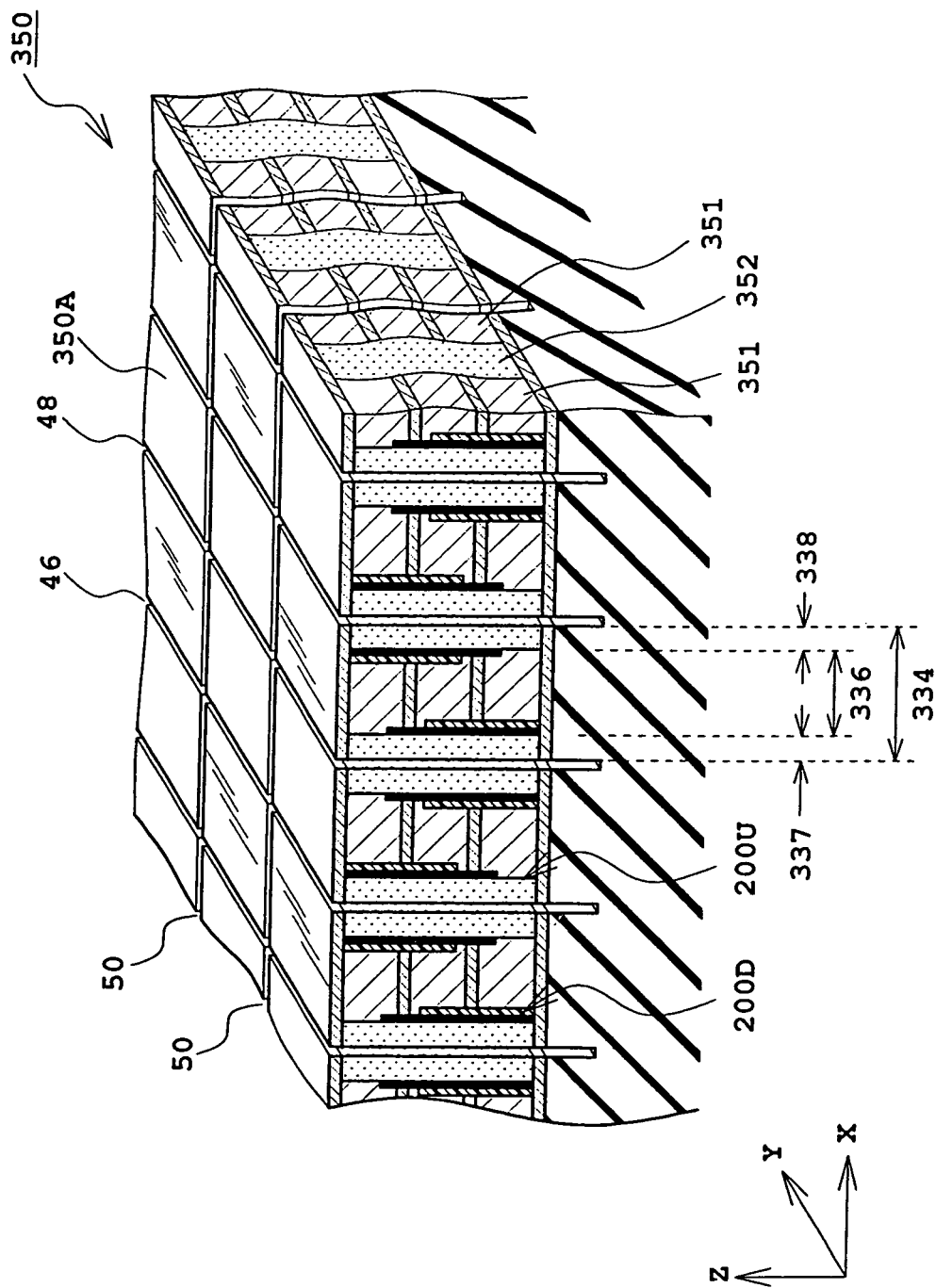
FIG. 34 is a perspective view showing one example of a layered 2D array transducer which is compounded in the X and Y directions.

FIG. 33 shows the manufacturing process in the form of a flow chart. When Y direction compounding is performed prior to X direction compounding with regard to a layered assembly, step 502 is performed through step S501 and then step S503 is performed. More specifically, at step S502, step S201 shown in FIG. 13 is performed, in which the Y direction compounding process is applied to a layered assembly (see FIGS. 17 and 18). Then, at step S503, steps S401 to S406 shown in FIG. 24 are performed, so that simultaneously with creation of a plurality of specified structures arranged in the X direction, a plurality of resin layers are also formed in the X direction. Thus, a layered assembly which is compounded in both the X and Y directions is formed.

When the Y direction compounding is performed after X direction compounding, on the other hand, step S504 is performed after step S501, and then step S505 is performed. Specifically, at step S504, steps S401 to S406 shown in FIG. 24 are performed (see FIG. 30). Then, at step S505, similar to steps S302 and S303 shown in FIG. 21, a plurality of compounding slits are formed in the Y direction and each slit is filled with a compounding resin material. Thus, a layered assembly which is compounded in both the X and Y directions is formed.

When a 1D array transducer (type A) is formed after the above-described two dimensional compounding, step S508 is performed through steps S506 and S507. At step S508, a plurality of separating slits are formed in the X direction. Each separating slit extends in the Y direction. As a result, a plurality of transducer elements arranged in the X direction are formed. These transducer elements are as shown in the structure shown in FIG. 34 which will be described below, but do not include the plurality of separating slits 50 of FIG. 34.

When a 2D array transducer (type A) is to be formed after the above-described two dimensional compounding, step S511 is performed through steps S506 and S510. At step S511, a plurality of separating slits are formed in the X and Y directions. Thus, a two dimensional array transducer as shown in FIG. 34 is formed. Specifically, a plurality of separating slits 46, 48 are formed on the two dimensionally combined layered assembly. Each separating slit 46, 48 extends in the Y direction and is formed for each specified structure 200U, 200D. When attention is paid to a certain transducer element 350A, the transducer element 350A is made up of a piezoelectric segment 336 and two resin segments 337, 338 formed on both sides of the piezoelectric segment 336, in the X direction. Numeral 334 denotes the overall width of the transducer element 350A in the X direction. The same transducer element 350A comprises two piezoelectric segments 351 and one resin segment 352 in the Y direction. Accordingly, when seen from above, the transducer element 350A is formed by the resin section having an H shape and two rectangular piezoelectric sections. The structure shown in FIG. 34 is only one example, and a desired number of piezoelectric segments and resin segments may be provided in the Y direction, for example.

When a 2D array transducer (type B) is to be formed after the above-described two dimensional compounding, step S512 is performed after steps S506 and S510. At step S512, a plurality of separating slits are formed by thinning out in the X direction and a plurality of separating slits are formed by thinning out in the Y direction. More specifically, a plurality of separating slits 48 are formed in the X direction on the layered assembly 350 which is two-dimensionally compounded. Each separating slit 48 extends in the Y direction and is formed for each specified structure 200D. Namely, in the example shown in FIG. 35, the separating slit 46 is not formed for each specified structure 200U (see FIG. 34). Of course, the formation of the separating slits is not limited to the example shown in FIG. 35 where the separating slit is formed for every other specified structures in the series of a plurality of specified structures, and the separating slit may be formed for every m (m is two or greater) specified structures. A plurality of separating slits 50, on the other hand, may be formed at desired intervals, and more piezoelectric segments 351 and more resin segments 352 may be provided for one transducer.

Figure 35:
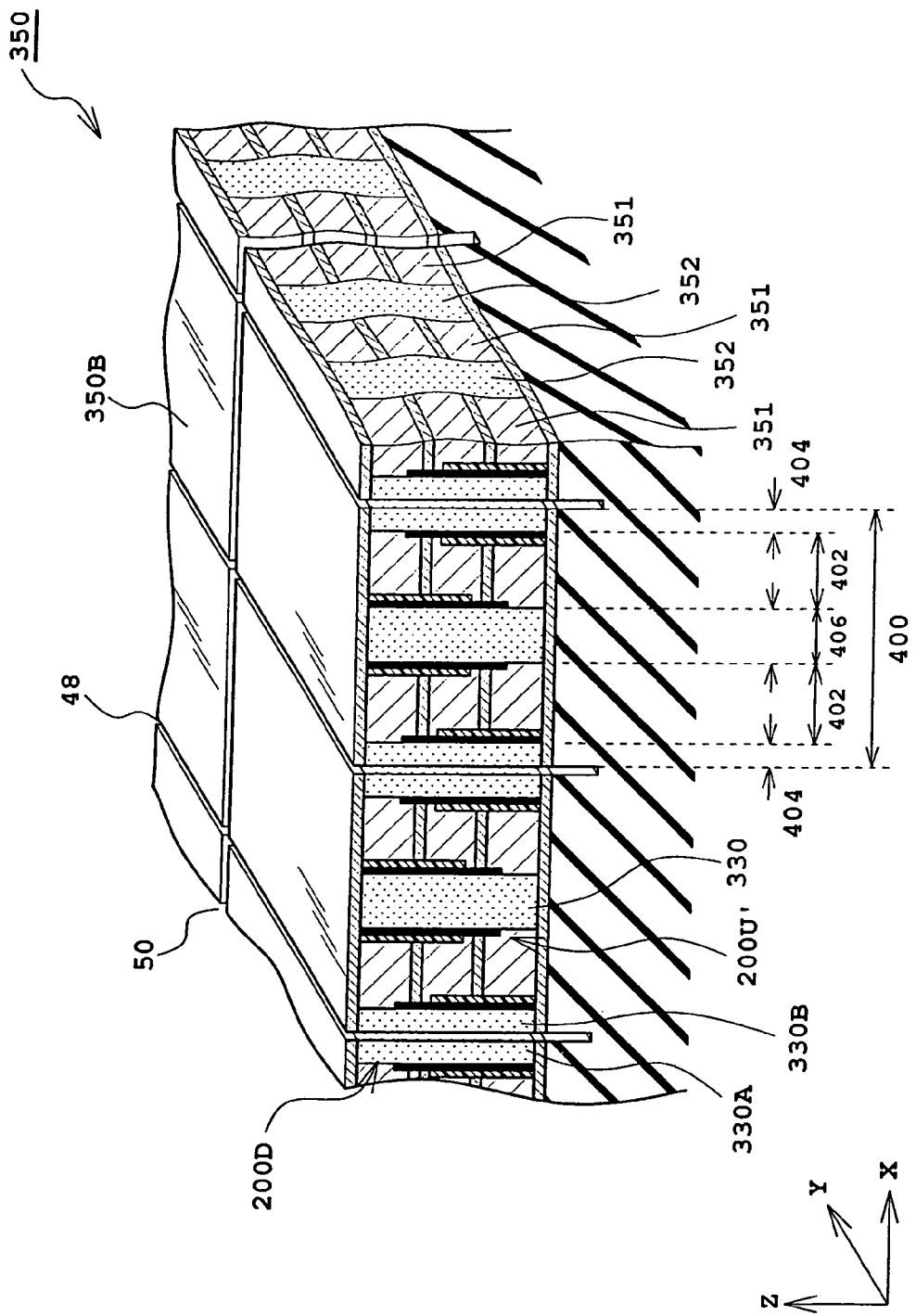
FIG. 35 is a perspective view showing another example of a layered 2D array transducer which is compounded in the X and Y directions.

In the example shown in FIG. 35, when attention is paid to a certain transducer element 350B, the transducer element 350B is made up of two piezoelectric segments 402, a resin segment 406 interposed between these piezoelectric segments 402, and two resin segments 404 formed on the outer sides of the two piezoelectric segments, in the X direction. Numeral 400 denotes the overall width of a transducer element 350B in the X direction. The same transducer element 350B is formed by three piezoelectric segments 351 and two resin segments 352 in the Y direction. Accordingly, when seen from above, the transducer element 350B is formed by 6 (=2×3) piezoelectric sections and a resin section having a lattice shape and formed between the piezoelectric segments. It should be noted that the structure shown in FIG. 35 is only one example, and it is also possible to provide more piezoelectric segments and more resin segments in the X and Y directions, for example.

In the example shown in FIG. 35, a specified structure 200D is formed between two transducer elements which are adjacent to each other in the X direction, and a specified structure 200U' is formed in the center portion of a transducer element 350B. When the specified structure (specified structure between elements) 200D and the specified structure (specified structure within element) 200U' are compared, they are different in that the specified structure 200D includes a separating slit 46 whereas the specified structure 200U' includes no separating slit, and they are similar to each other in that they both have a pair of vertical electrode layers having the same polarity which are symmetrical to each other. In particular, the specified structure 200D and the specified structure 200U' are similar in that they can achieve excellent insulating properties and that they can facilitate creation of the structure.

According to the above second to fifth examples, an array transducer in which both lamination and compounding has been performed can be achieved. In particular, because compounding is performed after lamination of layers, it is possible to eliminate a positioning error in the horizontal direction among the members arranged in the vertical direction. Further, compounding can be easily performed by forming a slit and filling the slit with a filler material.

While the preferred embodiments of the present invention have been described using specific terms, such description is for illustrative purposes only, and it is to be understood that changes and variations may be made without departing from the spirit or scope of the appended claims.

What is claimed is:

1. A method of manufacturing an ultrasonic probe, the method comprising the steps of:
   forming a plurality of first slits on a layered assembly having a first inner electrode member and a second inner electrode member from a top surface of the layered assembly and forming a plurality of second slits through a bottom surface of the layered assembly such that they are parallel to and alternate with the plurality of first slits;
   forming a first vertical electrode layer on each side surface within each of the first slits, the first vertical electrode layer being electrically connected with the first inner electrode member and being insulated with respect to the second inner electrode member, thereby forming a plurality of first specified structures corresponding to the plurality of first slits;

forming a second vertical electrode layer on each side surface within each of the second slits, the second vertical electrode layer being electrically connected with the second inner electrode member and being insulated with respect to the first inner electrode member, thereby forming a plurality of second specified structures corresponding to the plurality of second slits;

after formation of the plurality of first specified structures and the plurality of second specified structures, forming a plurality of separating slits on the layered assembly, thereby dividing the layered assembly into a plurality of transducer elements; and prior to the formation of the plurality of first slits and the plurality of second slits, performing compounding in the horizontal direction with respect to the layered assembly; and wherein the steps of performing compounding comprises the steps of:

forming a plurality of slits used for compounding in the layered assembly; and filling the plurality of slits used for compounding with a filler material.

2. A method of a manufacturing and ultrasonic probe, the method comprising the steps of:

forming a first plurality of slits on a layered assembly having a first inner electrode member and a second inner electrode member through a top surface of the layered assembly and forming a plurality of second slits through a bottom surface of the layered assembly such that they are parallel to and alternate with the plurality of first slits;

forming a first vertical electrode layer on each side surface within each of the first slits, the first vertical electrode layer being electrically connected with the first inner electrode member and being insulated with respect to the second inner electrode member thereby forming a plurality of first specified structures corresponding to the plurality of first slits;

forming a second vertical electrode layer on each side surface with each of the second slits, the second vertical electrode layer being electrically connected with second inner electrode member and being insulated with respect to the first inner electrode member, thereby forming a plurality of second specified structures corresponding to the plurality of second slits; and after formation, of the plurality of first specified structures and the plurality of second specified structures, forming a plurality of separating slits on the layered assembly, thereby dividing the layered assembly into a plurality of transducer elements; and wherein the step of forming the plurality of first specified structures and the plurality of second specified structures comprises the step of performing compounding and the horizontal direction with respect to the layered assembly.

3. The method according to claim 2, wherein the step of performing compounding in the horizontal direction with respect to the layered assembly is a step of filling the plurality of first slits and the plurality of second slits with a filler material used for compounding.

4. A method of manufacturing an ultrasonic probe, the method comprising the steps of:

forming a plurality of first slits in a layered assembly having a first inner electrode member and a second inner electrode member through a top surface of the layered assembly and forming a plurality of second slits through a bottom surface of the layered assembly such that they are parallel to and alternate with the plurality of first slits;

forming a first vertical electrode layer on each side surface within each of the first slits, the first vertical electrode layer being electrically connected with the first inner electrode member and being insulated with respect to the second inner electrode member, thereby forming a plurality of first specified structures corresponding to the plurality of first slits;

forming a second vertical electrode layer by a on each side surfrce within each of the second slits, the second vertical electrode layer being electrically connected with the second inner electrode member and being insulated with respect to the first inner electrode member, thereby forming a plurality of second specified structures corresponding to the plurality of second slits;

after formation of the plurality of first specified structures and the plurality of second specified structures, forming a plurality of separating slits on the layered assembly, thereby dividing the layered assembly into a plurality of transducer elements; and after formation of the plurality of first specified structures and the plurality of second specified structures, performing compounding in the horizontal direction with the respect to the layered assembly.

5. The method according to claim 4, wherein the step of performing compounding comprises the steps of:

providing a plurality of third slits used for compounding in the layered assembly; and filling the plurality third slits for compounding with a fill-in material.

6. A method of manufacturing an ultrasonic probe comprising the steps of:

forming a plurality of first slits having a first depth on a layered assembly comprising a first inner electrode member and a second inner electrode member through a top surface of the layered assembly;

forming a plurality of second slits having a second depth on the layered assembly through a bottom surface of the layered assembly, such that the plurality of second slits are parallel to and alternate with the plurality of first slits;

filling the plurality of first slits and the plurality of second slits with an insulating material and hardening the insulating material;

forming a plurality of third slits by cutting through the insulating material within the plurality of first slits, the plurality of third slits having a width which allows the insulating material which is hardened to be left on each side surface of each of the first slits and having a third depth which is greater than the first depth;

forming a plurality of fourth slits by cutting through the insulating material within the plurality of second slits, the plurality of fourth slits having a width which allows the insulating material which is hardened to be left on each side surface of each of the second slits and having a fourth depth which is greater than the second depth;

forming a first vertical electrode layer electrically connected with the first inner electrode member on each side surface of each of the third slits, thereby forming a plurality of first specified structures on the layered assembly;

forming a second vertical electrode layer electrically connected with the second inner electrode member on each side surface of each of the fourth slits, thereby forming a plurality of second specified structures on the layered assembly;

after formation of the plurality of first specified structures and the plurality of second specified structures, forming a top electrode member on a top surface of the layered assembly and forming a bottom electrode member on a bottom surface of the layered assembly;

bonding a backing to the bottom electrode member; and after bonding of the backing, dividing the layered assembly into a plurality of transducer elements.

7. The method according to claim 6, wherein the step of forming the plurality of first specified structures includes a step of, after formation of the first vertical electrode layer on each side surface within each of the third slits, filling the plurality of third slits with a reinforcing material or a resin material used for compounding and hardening the material; and the step of forming the plurality of second specified structures includes a step of, after formation of the second vertical electrode layer on each side surface within each of the fourth slits, filling the plurality of fourth slits with a reinforcing material or a resin material used for compounding and hardening the material.

* * * * *